US010379124B2

(12) United States Patent
Yu et al.

(10) Patent No.: US 10,379,124 B2
(45) Date of Patent: Aug. 13, 2019

(54) TUMOR SUPPRESSOR VSTM2A AS A BIOMARKER FOR COLORECTAL CANCER

(71) Applicant: The Chinese University of Hong Kong, Shatin (CN)

(72) Inventors: Jun Yu, Hong Kong (CN); Joseph Jao Yiu Sung, Hong Kong (CN); Simon Siu Man Ng, Hong Kong (CN); Yujuan Dong, Hong Kong (CN)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 0 days.

(21) Appl. No.: 15/480,107

(22) Filed: Apr. 5, 2017

(65) Prior Publication Data

US 2018/0267042 A1 Sep. 20, 2018

Related U.S. Application Data

(60) Provisional application No. 62/473,134, filed on Mar. 17, 2017.

(51) Int. Cl.

| | |
|---|---|
| ***C12Q 1/68*** | (2018.01) |
| ***G01N 33/574*** | (2006.01) |
| ***C12P 19/34*** | (2006.01) |
| ***C12Q 1/6886*** | (2018.01) |
| *C12Q 1/00* | (2006.01) |
| *G01N 33/00* | (2006.01) |

(52) U.S. Cl.

CPC ........ *G01N 33/57419* (2013.01); *C12P 19/34* (2013.01); *C12Q 1/6886* (2013.01); *C12Q 1/00* (2013.01); *C12Q 2600/154* (2013.01); *C12Q 2600/158* (2013.01); *G01N 33/00* (2013.01); *G01N 2800/50* (2013.01); *G01N 2800/56* (2013.01)

(58) Field of Classification Search

None

See application file for complete search history.

(56) References Cited

PUBLICATIONS

Choi et al., "Epigenetic Alterations in Gastric Carcinogenesis," Cell Research, 15(4):247-254 (Apr. 2005).

Livak et al., "Analysis of Relative Gene Expression Data Using Real-Time Quantitative PCR and the $2^{-\Delta\Delta C}{}_T$ Method," Methods 25, 402-408 (2001).

Takai et al., "Comprehensive Analysis of CpG Islands in Human Chromosomes 21 and 22," PNAS, vol. 99, No. 6, Mar. 19, 2002, 3740-3745.

Takai, et al., "The CpG Island Searcher: A New WWW Resource," In Silico Biology 3, (2003), 235-240.

*Primary Examiner* — Katherine D Salmon

(74) *Attorney, Agent, or Firm* — Kilpatrick Townsend & Stockton LLP

(57) ABSTRACT

The present invention provides a method for diagnosing and determining prognosis of colorectal cancer in a subject by detecting suppressed expression of the VSTM2A gene, which in some cases is due to elevated methylation level in the genomic sequence of this gene. A kit and device useful for such a method are also provided. In addition, the present invention provides a method for treating colorectal cancer by increasing VSTM2A gene expression or activity.

10 Claims, 14 Drawing Sheets

Specification includes a Sequence Listing.

SEQUENCE LISTING

```
<160> NUMBER OF SEQ ID NOS: 26

<210> SEQ ID NO 1
<211> LENGTH: 22
<212> TYPE: DNA
<213> ORGANISM: Homo sapiens

<400> SEQUENCE: 1

ggaccaagat cagcacagtg aa                                               22


<210> SEQ ID NO 2
<211> LENGTH: 23
<212> TYPE: DNA
<213> ORGANISM: Homo sapiens

<400> SEQUENCE: 2

tcatcctttt tcctcacttt gga                                              23


<210> SEQ ID NO 3
<211> LENGTH: 21
<212> TYPE: DNA
<213> ORGANISM: Homo sapiens

<400> SEQUENCE: 3

acctccagcc ctcaagtggt a                                                21


<210> SEQ ID NO 4
<211> LENGTH: 21
<212> TYPE: DNA
<213> ORGANISM: Homo sapiens

<400> SEQUENCE: 4

cctttctgtg gagcgtttgt g                                                21


<210> SEQ ID NO 5
<211> LENGTH: 23
<212> TYPE: DNA
<213> ORGANISM: Homo sapiens

<400> SEQUENCE: 5

tctccaatcc ttccagaagt caa                                              23


<210> SEQ ID NO 6
<211> LENGTH: 21
<212> TYPE: DNA
<213> ORGANISM: Homo sapiens
```

```
<400> SEQUENCE: 6

tctgtgtgac gttgggaagg t                                              21


<210> SEQ ID NO 7
<211> LENGTH: 21
<212> TYPE: DNA
<213> ORGANISM: Homo sapiens

<400> SEQUENCE: 7

acctccagcc ctcaagtggt a                                              21


<210> SEQ ID NO 8
<211> LENGTH: 22
<212> TYPE: DNA
<213> ORGANISM: Homo sapiens

<400> SEQUENCE: 8

acaaagccac aaacaagaag ca                                             22


<210> SEQ ID NO 9
<211> LENGTH: 22
<212> TYPE: DNA
<213> ORGANISM: Homo sapiens

<400> SEQUENCE: 9

acaatcagca aagagcaaat cg                                             22


<210> SEQ ID NO 10
<211> LENGTH: 20
<212> TYPE: DNA
<213> ORGANISM: Homo sapiens

<400> SEQUENCE: 10

gcaggcgctc cttgtgtagt                                                20


<210> SEQ ID NO 11
<211> LENGTH: 18
<212> TYPE: DNA
<213> ORGANISM: Homo sapiens

<400> SEQUENCE: 11

gtcttcccct ccatcgtg                                                  18


<210> SEQ ID NO 12
<211> LENGTH: 20
<212> TYPE: DNA
<213> ORGANISM: Homo sapiens

<400> SEQUENCE: 12

agggtgagga tgcctctctt                                                20


<210> SEQ ID NO 13
<211> LENGTH: 23
<212> TYPE: DNA
<213> ORGANISM: Homo sapiens

<400> SEQUENCE: 13

ctcggtgtat ctggagatcc aat                                            23


<210> SEQ ID NO 14
<211> LENGTH: 20
<212> TYPE: DNA
<213> ORGANISM: Homo sapiens
```

<400> SEQUENCE: 14
cccgtagttg gcatcagtca 20

<210> SEQ ID NO 15
<211> LENGTH: 24
<212> TYPE: DNA
<213> ORGANISM: Homo sapiens

<400> SEQUENCE: 15
tgttttttag aagggagatt ttag 24

<210> SEQ ID NO 16
<211> LENGTH: 30
<212> TYPE: DNA
<213> ORGANISM: Homo sapiens

<400> SEQUENCE: 16
tacctaacta cctactttca actacctaac 30

<210> SEQ ID NO 17
<211> LENGTH: 406
<212> TYPE: DNA
<213> ORGANISM: Homo sapiens

<400> SEQUENCE: 17
cggaaccttt tgctccgagc cccccgccag cgccgcaatc ccgtcactgt attgtcctcc 60
tcggcaccga gcgatctgat ccgccgagcc agaaagacac ccgatggggg agagaagcaa 120
agtggaaaaa aaccgacgtc cctgctctcc agaagggaga ccccagcggc gccgacgagc 180
cctgcgccct ccgcggccgc ccggcgcgag ctcccgggcg gggcgctgtc cagcgcgcac 240
agagttaaag gcatcatcgc agccattaga gggaaaagtt gcggcgccgc gagcccggcg 300
aagtcctcag cccgccccgc ttgcccactc cccacttccc gagccggctc cgtgtttagg 360
gagggcagtg atcacgcaag ccggagcggc gggctgacgt tggacg 406

<210> SEQ ID NO 18
<211> LENGTH: 723
<212> TYPE: DNA
<213> ORGANISM: Homo sapiens

<400> SEQUENCE: 18
atgatgggga tctttttggt gtatgttgga tttgttttct tttccgtttt atatgtacaa 60
caagggcttt cttctcaagc aaaatttacc gagtttccgc ggaacgtgac ggcgaccgag 120
gggcagaatg tggagatgtc ctgcgccttc cagagcggct ccgcctcggt gtatctggag 180
atccaatggt ggttcctgcg ggggccggag gacctggatc ccggggccga gggggccggc 240
gcgcaggtgg agctcttgcc cgacagagac ccggacagcg acgggaccaa gatcagcaca 300
gtgaaagtcc aaggcaatga catctcccac aagcttcaga tttccaaagt gaggaaaaag 360
gatgaaggct tatatgagtg cagggtgact gatgccaact acggggagct tcaggaacac 420
aaggcccagg cctatctgaa agtcaatgcc aacagccatg cccgcagaat gcaggccttc 480
gaagcctcgc ccatgtggct gcaggatatg aagccccgca agaacgtctc cgcagccatc 540
cccagcagca tccatggctc tgccaaccaa cgaacgcact ccacctccag ccctcaagtg 600
gtagccaaaa tccccaaaca aagtccacaa tcagcaaaga gcaaatcgcc tgtaaaatct 660
acggagcgga cagcaaagtt gaccctaaac tccaagcacc accctgcacc cactgtactc 720
taa 723

<210> SEQ ID NO 19
<211> LENGTH: 3000
<212> TYPE: DNA
<213> ORGANISM: Homo sapiens

<400> SEQUENCE: 19

```
gcgccgcgag cccggcgaag tcctcagccc gccccgcttg cccactcccc acttcccgag      60
ccggctccgt gtttagggag ggcagtgatc acgcaagccg gagcggcggg ctgacgttgg     120
acgagctgcc aggtagctga aagcaggcag ccaggcagcc gagacacttc ccagcgattc     180
cagcctgggc tccgcaggaa gcctcgctga atcccagcca gctggttcta accttccaga     240
atcgcaatcc cttctcccca cagccagccc tcgccaagca agcagcagga tgtttgcagt     300
gtcgcgccca gggctctgag actgagcctg ccatccactc gcacgccttt ctttcagggc     360
ttttcggctg ttggctacac tgatgtgacc cccctccctt tttggaatga tggggatctt     420
tttggtgtat gttggatttg ttttcttttc cgttttatat gtacaacaag ggctttcttc     480
tcaagcaaaa tttaccgagt ttccgcggaa cgtgacggcg accgaggggc agaatgtgga     540
gatgtcctgc gccttccaga gcggctccgc ctcggtgtat ctggagatcc aatggtggtt     600
cctgcggggg ccggaggacc tggatcccgg ggccgagggg gccggcgcgc aggtggagct     660
cttgcccgac agagacccgg acagcgacgg gaccaagatc agcacagtga aagtccaagg     720
caatgacatc tcccacaagc ttcagatttc caaagtgagg aaaaaggatg aaggcttata     780
tgagtgcagg gtgactgatg ccaactacgg ggagcttcag gaacacaagg cccaggccta     840
tctgaaagtc aatgccaaca gccatgcccg cagaatgcag gccttcgaag cctcgcccat     900
gtggctgcag gatatgaagc ccgcaagaa cgtctccgca gccatcccca gcagcatcca      960
tggctctgcc aaccaacgaa cgcactccac ctccagccct caagtggtag ccaaaatccc    1020
caaacaaagt ccacaatcag caaagagcaa atcgcctgta aaatctacgg agcggacagc    1080
aaagttgacc ctaaactcca agcaccaccc tgcacccact gtactctaat tcactacaca    1140
aggagcgcct gcttccggaa gcataaatga agaggctatc acatgctttg ttgatcatat    1200
tttctttggc aaaacactga tcttttattt taagagaatt aacgtgaagt gatagaacgt    1260
tttctaatag caagatctat tttttccctt ttctttcggc gactaaaatc atctcactga    1320
ctgctcaagg gttggcctga atgtcatcag gatagggaat atttactatg gataccacta    1380
atttcctact aaaggaccca gcatcttcag gaagcaaaca gagatcaaaa ggctacagaa    1440
cagaagctat catcagacaa aaccccccttt ttaggggaag aacaaaacta tcaacactgc   1500
aagtcaacaa ggaggacatt actttaagga ataacatgag aaagaaattt ttttattttc    1560
ccctttttttt cttggatttt tcttcttttt cttgattaca gttcttgttc aatggtggca   1620
agtgctggtt atggccaatc tccgtcaatc ctaggaggtt tatagaacta cattttgagt    1680
gttctatatt tcagtgtatt ttaattcatt ttgcaattcc tgtgtatgca aacctgataa    1740
attctgtaaa ttgcttatag tatgtgtgct ataacttcaa agtagatgta ctgcgaccct    1800
catgcaagct gatttttatc attatatata taaatatata cttaagaata tctgtgtgtt    1860
gggccaatga ccaacttttt ttgacgaagc atttgttttt cgttgataat tcatacactg    1920
cgtgaatttt gtaattcatt gtttcacttc cacaggtttg acagctgcag atggtctcta    1980
ttgtcctctg cttcattctg gaaagtgcat attcaaaatt gtatcagtct ctgatcgatg    2040
aattaatttt gttatgtctg tgctaagttg gaatttacta tgttccttta tacatggtgt    2100
ttattgaggt ttgagagtct cttgactgtg aagaatgtac actgtctggt tttgacagct    2160
```

```
atttctgtat tattatcatt ataatcttgt caaatagaaa tgttgcttct agaaaatttg   2220

cctaggaggc gaatgtgggg aaggtgaagc actcaccata attccctaaa ttcatgttag   2280

aacatttctt gctatggtta aaaatgctgc ttcctttgac ctttatgaat ttctgtacct   2340

ttgtcattct gttacctttg tcattctgtt atttgcgcta attatatttt aatgtctcct   2400

aattaaaaat taaaatttgg ttgttggcta aatacaatat gcaaaagatg atggcaggtc   2460

cccgactaaa gaagattaat gtgttcagtt ttcactggtt aagtgaatta taattttaaa   2520

tattccattc ttatttatgt ctttatgata attcagacta ttttattttg aacctgtttt   2580

ctactctggc aaagaaagat aggcagaact attagtgttc catatacatt atggaataga   2640

taaagcttga gagataaatg acctaagttt tccttccaga gagactcttc cattttctct   2700

cattacaaaa ccagaagatc agctatgtgg ggccatcagc tcccagccta aggtcctata   2760

acccgaagct tgaaggcaat cagtacctct gcttttcaaa ggtaaatgca ttcattttct   2820

ttgattcagt tataagcaag tatatatttt cataatattc ttgacattac ctgagaaata   2880

atacttcatg ctaaatcttt tactgccact tttctcattc atttggttta tcatttcagt   2940

ttaatgagaa aaattaataa aggttttgat tgcactattt tattaaccta aaaaaaaaaa   3000
```

```
<210> SEQ ID NO 20
<211> LENGTH: 82
<212> TYPE: DNA
<213> ORGANISM: Homo sapiens

<400> SEQUENCE: 20

ggaccaagat cagcacagtg aaagtccaag gcaatgacat ctcccacaag cttcagattt     60

ccaaagtgag gaaaaaggat ga                                              82
```

```
<210> SEQ ID NO 21
<211> LENGTH: 153
<212> TYPE: DNA
<213> ORGANISM: Homo sapiens

<400> SEQUENCE: 21

acctccagcc ctcaagtggt agccaaaatc cccaaacaaa gtccacaatc aggtatggaa     60

acccatttcg agccttttat tttaccactc acaaacgctc cacagaaagg tcagtcgtat    120

agagtagaca gatttatgaa tggtgatttt taa                                 153
```

```
<210> SEQ ID NO 22
<211> LENGTH: 120
<212> TYPE: DNA
<213> ORGANISM: Homo sapiens

<400> SEQUENCE: 22

tctccaatcc ttccagaagt caaacatctc cacagaccac ctctactagt ccttcctttc     60

ttctctctgt cttcactttt ttctactgac ccccttccca ccttcccaac gtcacacaga    120
```

```
<210> SEQ ID NO 23
<211> LENGTH: 110
<212> TYPE: DNA
<213> ORGANISM: Homo sapiens

<400> SEQUENCE: 23

acctccagcc ctcaagtggt agccaaaatc cccaaacaaa gtccacaatc aggtgcgagg     60

atagctacaa gccatggact ttctgtcctg cttcttgttt gtggctttgt               110
```

<210> SEQ ID NO 24
<211> LENGTH: 120
<212> TYPE: DNA
<213> ORGANISM: Homo sapiens

<400> SEQUENCE: 24
acaatcagca aagagcaaat cgcctgtaaa atctacggag cggacagcaa agttgaccct 60
aaactccaag caccaccctg cacccactgt actctaattc actacacaag gagcgcctgc 120

<210> SEQ ID NO 25
<211> LENGTH: 241
<212> TYPE: DNA
<213> ORGANISM: Homo sapiens

<400> SEQUENCE: 25
ctcggtgtat ctggagatcc aatggtggtt cctgcggggg ccggaggacc tggatcccgg 60
ggccgagggg gccggcgcgc aggtggagct cttgcccgac agagacccgg acagcgacgg 120
gaccaagatc agcacagtga aagtccaagg caatgacatc tcccacaagc ttcagatttc 180
caaagtgagg aaaaaggatg aaggcttata tgagtgcagg gtgactgatg ccaactacgg 240
g 241

<210> SEQ ID NO 26
<211> LENGTH: 240
<212> TYPE: PRT
<213> ORGANISM: Homo sapiens

<400> SEQUENCE: 26

Met Met Gly Ile Phe Leu Val Tyr Val Gly Phe Val Phe Phe Ser Val
1 5 10 15

Leu Tyr Val Gln Gln Gly Leu Ser Ser Gln Ala Lys Phe Thr Glu Phe
20 25 30

Pro Arg Asn Val Thr Ala Thr Glu Gly Gln Asn Val Glu Met Ser Cys
35 40 45

Ala Phe Gln Ser Gly Ser Ala Ser Val Tyr Leu Glu Ile Gln Trp Trp
50 55 60

Phe Leu Arg Gly Pro Glu Asp Leu Asp Pro Gly Ala Glu Gly Ala Gly
65 70 75 80

Ala Gln Val Glu Leu Leu Pro Asp Arg Asp Pro Asp Ser Asp Gly Thr
85 90 95

Lys Ile Ser Thr Val Lys Val Gln Gly Asn Asp Ile Ser His Lys Leu
100 105 110

Gln Ile Ser Lys Val Arg Lys Lys Asp Glu Gly Leu Tyr Glu Cys Arg
115 120 125

Val Thr Asp Ala Asn Tyr Gly Glu Leu Gln Glu His Lys Ala Gln Ala
130 135 140

Tyr Leu Lys Val Asn Ala Asn Ser His Ala Arg Arg Met Gln Ala Phe
145 150 155 160

Glu Ala Ser Pro Met Trp Leu Gln Asp Met Lys Pro Arg Lys Asn Val
165 170 175

Ser Ala Ala Ile Pro Ser Ser Ile His Gly Ser Ala Asn Gln Arg Thr
180 185 190

His Ser Thr Ser Ser Pro Gln Val Val Ala Lys Ile Pro Lys Gln Ser
195 200 205

-continued

```
Pro Gln Ser Ala Lys Ser Lys Ser Pro Val Lys Ser Thr Glu Arg Thr
    210                 215                 220

Ala Lys Leu Thr Leu Asn Ser Lys His His Pro Ala Pro Thr Val Leu
225                 230                 235                 240
```

TUMOR SUPPRESSOR VSTM2A AS A BIOMARKER FOR COLORECTAL CANCER

CROSS REFERENCE TO RELATED APPLICATION

This application claims the benefit of U.S. Provisional Application No. 62/473,134, filed Mar. 17, 2017, the entire contents of which is incorporated herein by reference.

REFERENCE TO SUBMISSION OF A SEQUENCE LISTING AS A TEXT FILE

The Sequence Listing written in file SequenceListing_1045551.txt created on Jun. 30, 2017, 12,139 bytes, machine format IBM-PC, MS-Windows operating system, is hereby incorporated by reference in its entirety for all purposes.

BACKGROUND OF THE INVENTION

Colorectal cancer is the third most common cancer worldwide, accounting for about 10% of all cancer cases diagnosed annually. It is a deadly disease with serious impact on human health. During the year of 2012, for instance, 1.4 million new cases of colorectal cancers were diagnosed globally, and nearly 700,000 deaths from the disease were recorded. Incidence of colorectal cancers is substantially higher in developed countries, where more than 65% of cases are found. Men are more likely to suffer from this disease than women.

Diagnosis of colorectal cancer can be challenging. Although family history may provide useful implications for diagnosis, vast majority of the disease (greater than 75-95%) occurs in people with little or no genetic risk. Symptoms of colorectal cancer also can vary significantly, depending on the location of the cancer in the colon, and whether it has spread elsewhere in the body. Depending on how early colorectal cancer is diagnosed, its prognosis can vary from very good to very grim: it is highly curable with surgery when the cancer mass remains confined within the wall of the colon; on the other hand, once colorectal cancer has spread, it is usually not curable, with medical intervention focusing on improving quality of life and alleviating symptoms. On average, the 5-year survival rate in the United States is around 65%.

Because of the high prevalence of colorectal cancer and the vital importance of early diagnosis on patients' life expectancy, there exists an urgent need for new and more effective methods to diagnose, monitor, and treat colorectal cancer. This invention fulfills this and other related needs.

BRIEF SUMMARY OF THE INVENTION

The present inventors have identified VSTM2A as a novel tumor suppressor and diagnostic/prognostic marker for human colorectal cancer. More specifically, the inventors show that, compared with normal individuals, CpG islands of the VSTM2A gene (especially in the promoter region) are hypermethylated in biological samples of cancer tissues from colorectal cancer patients. Such hypermethylation leads to VSTM2A silencing at both mRNA and protein levels. Restoration of VSTM2A expression inhibits cancer cell growth and induces programmed cell death. Protein/mRNA expression level of VSTM2A and promoter methylation level of VSTM2A genetic sequence closely correlate with the survival of colorectal cancer patients and are therefore also useful as prognostic markers for colorectal cancer.

As such, in the first aspect, the present invention provides a method for assessing the risk for colorectal cancer in a subject, i.e., the likelihood of colorectal cancer being present in the subject and/or the likelihood of the subject developing the disease at a later time. The method includes the steps of: (a) measuring expression level of VSTM2A in a sample taken from the subject, and (b) comparing the expression level obtained in step (a) with a standard control. When a decrease in the expression level of VSTM2A is detected as compared with the standard control, it indicates that the subject may have colorectal cancer or have an increased risk for colorectal cancer. Typically, the sample used in the method is a colon mucosa sample, e.g., one that includes colon epithelial cells. The subject being tested may be a human or a member of other mammals such as primates, who may or may not exhibit any signs indicative of any condition or abnormality relating to the colon.

In some embodiments, the expression level of VSTM2A is the VSTM2A protein level. In other embodiments, the expression level of VSTM2A is VSTM2A mRNA level. When the VSTM2A protein level is measured, step (a) may include an immunoassay using an antibody that specifically binds the VSTM2A protein. For example, a Western Blot analysis may be used. In other cases, step (a) may involve mass spectrometry, or a hybridization-based assay such as hybridization to a microarray, fluorescence probe, or molecular beacon.

When VSTM2A mRNA level is measured, step (a) in some cases may involve an amplification reaction, such as a polymerase chain reaction (PCR), especially a reverse transcriptase-PCR (RT-PCR). In other cases, the detecting step may involve a polynucleotide hybridization assay, such as a Southern Blot analysis or Northern Blot analysis or an in situ hybridization assay. For example, a polynucleotide probe may be used in the polynucleotide hybridization assay to hybridize with at least a segment of SEQ ID NO:18 or 19 or a complement thereof. In some cases, the polynucleotide probe may include a detectable moiety.

In some embodiments, when the subject is indicated as having colorectal cancer or having an increased risk of colorectal cancer after the first round of method steps described above, the claimed method may further include repeating the same steps at a later time using the same type of sample from the subject. An increase in the expression level of VSTM2A at the later time as compared to the amount from the original step (a) indicates an improvement of colorectal cancer or a lessened risk for the disease, whereas a decrease indicates a worsening of colorectal cancer or a heightened risk for the disease.

In a second aspect, the present invention provides another method for detecting colorectal cancer or assessing risk of colorectal cancer in a subject. The method includes the steps of: (a) treating a sample taken from the subject with an agent that differentially modifies methylated and unmethylated DNA; and (b) determining whether each CpG in a CpG-containing genomic sequence is methylated or unmethylated, thus determining the number of methylated CpGs within this sequence, with the CpG-containing genomic sequence being at least a segment of SEQ ID NO:17 and comprising at least 1, 2, 3, 4, 5, 10, 15, 20, 25, 50 or more CpG pairs. When the presence of at least one, or at least 5, or at least 12 methylated CpGs (for example, at least 50% of total CpGs), is detected in the CpG-containing genomic sequence, it indicates that the subject may have colorectal cancer or is at an increased risk of developing the disease. In some cases, the number of methylated CpGs is compared with a control number, e.g., the number of methylated CpGs in the same genomic sequence determined following the same process described above using a sample of the same type from non-cancerous tissue originated from a healthy control subject who has been determined as having no colorectal cancer or no known risk for the disease. When the number of methylated CpGs is higher in the test subject compared to the control number, the test subject is determined as having colorectal cancer or having an increased risk for the disease; otherwise the test subject is determined as not having colorectal cancer or not having any elevated risk for developing the disease.

In some embodiments, the CpG-containing genomic sequence contains two or more CpGs (e.g., up to 20, 25, 30, 40, or 50 CpGs), and when at least 50% of all CpGs being highly methylated (for example, at least 12 of 25 CpGs in the 167-319 segment of SEQ ID NO:17 being highly methylated or nearly 100% methylated) or when at least 90% of all CpGs being at least 50% methylated (for example, at least 22 of 25 CpGs in the 167-319 segment of SEQ ID NO:17 being moderately methylated or 50-100% methylated), the subject is indicated as having or at an increased risk for colorectal cancer. In some cases, the CpG-containing genomic sequence is a segment of at least 15, 20, 50, 100, 125, 150, 200, 250, 300, 400 or more contiguous nucleotides of SEQ ID NO:17. In other cases, the CpG-containing genomic sequence is SEQ ID NO:17 or the 167-319 segment of SEQ ID NO:17. In one embodiment of the claimed method, the CpG-containing genomic sequence is the 167-319 segment of SEQ ID NO:17, and when at least 5, 10, 12, 15, 20, 22, or 23 of all CpGs in this CpG-containing genomic sequence are methylated (at least 50% and up to 100% methylated), the subject is indicated as having colorectal cancer or having an increased risk for colorectal cancer.

In some examples, the sample used in the claimed method is a colon mucosa sample. In other examples, when the subject is indicated as having colorectal cancer after the first round of method steps described above, the method further involves repeating steps (a) and (b) at a later time using the sample type of sample from the subject. When an increase is detected in the number of methylated CpGs at the later time as compared to the number of methylated CpGs determined from the original step (b), it indicates a worsening of colorectal cancer, whereas a decrease indicates an improvement of colorectal cancer.

In some embodiments, the agent used in the claimed method to differentially modify methylated DNA and unmethylated DNA is an enzyme that preferentially cleaves methylated DNA, an enzyme that preferentially cleaves unmethylated DNA, or a bisulfite (e.g., sodium bisulfite). In other embodiments, step (b) of the method involves an amplification reaction; or step (b) may involve sequencing of a DNA molecule.

In a third aspect, the present invention provides a method for assessing likelihood of mortality in a colorectal cancer patient. The method includes the steps of: (a) treating a sample taken from a colorectal cancer patient, who has received a diagnosis of colorectal cancer, with an agent that differentially modifies methylated and unmethylated DNA; and (b) determining whether each CpG in a CpG-containing genomic sequence is methylated or unmethylated, thus determining the number of methylated CpGs within this sequence, with the CpG-containing genomic sequence being at least a segment of SEQ ID NO:17 (e.g., the 167-319 fragment of SEQ ID NO:17) and comprising at least 1, 2, 3, 4, 5, 10, 15, 20, 25, 30, 40, 50, or more CpG pairs. When the presence of at least 1 or 2, 3 or 4, or at least 5, 7, 10, or 12 methylated CpGs (for example, at least 50% of total CpGs), is detected in the CpG-containing genomic sequence, it indicates that the subject has a high likelihood of mortality (e.g., more likely than not, or greater than 10%, 20%, 30%, 40%, 50%, 60%, 70%, 80%, or 90% chance of mortality) in a subsequent time period, e.g., 1, 2, 3, 4, or 5 years or up to 10 years. In some cases, the likelihood of mortality is compared between two subjects who both have received a diagnosis of colorectal cancer. The number of methylated CpGs determined from the first patient's sample after steps (a) and (b) is then compared with the number of methylated CpGs in the same genomic sequence determined following the same process using a sample of the same type originated from the second patient. When the number of methylated CpGs is higher in the first patient's sample compared to the number in the second patient's sample, the first patient is determined as having a higher likelihood of mortality due to colorectal cancer than the second patient in a subsequent time period, e.g., 1, 2, 3, 4, or 5 years or up to 10 years. In some cases, the comparison is made between one test patient and an established low mortality patient who has been previously determined to have no or a very low number (e.g., 1 or 2) or a very low percentage (e.g., 5% or 10% or less) of methylated CpGs among all CpGs in the genomic sequence. When the test subject is found to have more methylated CpGs (especially when comparing the number of CpGs in comparable methylation level, for example, 50-100% methylation level or 100% methylation level) than the low mortality patient in the same genomic region, after both patients' samples have been processed through the method steps describe above, the test patient is deemed to have a higher likelihood of mortality due to colorectal cancer than the low mortality patient for a subsequent time period of, e.g., 1, 2, 3, 4, or 5 years or up to 10 years.

In some embodiments, the CpG-containing genomic sequence analyzed in this method contains two or more CpGs, for example, 10, 20, 25, 30, 50 or more, CpGs. In some cases, the CpG-containing genomic sequence is a segment of at least 15, 20, 50, 100, 125, 150, 200, 300, 400, or more contiguous nucleotides of SEQ ID NO:17. In other cases, the CpG-containing genomic sequence is SEQ ID NO:17, or the 167-319 fragment of SEQ ID NO:17 (corresponding to −117 to +36 segment in FIG. 2).

In some examples, the sample used in the claimed method is a colon mucosa sample. In some embodiments, the agent used in the claimed method to differentially modify methylated DNA and unmethylated DNA is an enzyme that preferentially cleaves methylated DNA, an enzyme that preferentially cleaves unmethylated DNA, or a bisulfite (e.g., sodium bisulfite). In other embodiments, step (b) of the method involves an amplification reaction such as a PCR; or step (b) may involve sequencing of a DNA molecule. In some embodiments, the PCR is performed using at least one primer consisting of the sequence set forth in any one of SEQ ID NOs:1-16 and 20-25, in combination with one or more other primer(s) appropriate for the amplification reaction.

In a related application of this invention, likelihood of mortality in a colorectal cancer patient due to the disease can also be assessed by comparing the expression level of VSTM2A mRNA or protein among patients who have been diagnosed with colorectal cancer. Briefly, the method for assessing likelihood of mortality includes the steps of: (a) measuring expression level of VSTM2A in a sample taken from a first patient who has been diagnosed with colorectal cancer, and (b) comparing the expression level obtained in step (a) with the expression level of VSTM2A determined in a sample of same type that was taken from a second colorectal cancer patient and measured in the same step (a). When the expression level of VSTM2A is lower in the first patient's sample than that found in the second patient's sample, the first patient is deemed as having a higher likelihood of mortality from colorectal cancer than the second patient. Typically, the sample used in the method is a colon mucosa sample, e.g., one that includes colon epithelial cells. The subject being tested may be a human or a member of other mammals such as primates. In some cases, the second patient is one who has been diagnosed with colon cancer but has been previously determined as having a normal expression level of VSTM2A mRNA and/or protein in the colon cancer tissue.

In some embodiments of this method, the expression level of VSTM2A is the VSTM2A protein level. In other embodiments, the expression level of VSTM2A is VSTM2A mRNA level. When the VSTM2A protein level is measured, step (a) may include an immunoassay using an antibody that specifically binds the VSTM2A protein. For example, a Western Blot analysis may be used. In other cases, step (a) may involve mass spectrometry, or a hybridization-based assay such as hybridization to a microarray, fluorescence probe, or molecular beacon.

When VSTM2A mRNA level is measured, step (a) in some cases may involve an amplification reaction, such as a PCR, especially an RT-PCR. In other cases, the detecting step may involve a polynucleotide hybridization assay, such as a Southern Blot analysis or Northern Blot analysis or an in situ hybridization assay. For example, a polynucleotide probe may be used in the polynucleotide hybridization assay to hybridize with at least a segment of SEQ ID NO:18 or 19 or a complement thereof. In some cases, the polynucleotide probe may include a detectable moiety. The sample used in this method is a colon mucosa sample taken from confirmed cancerous tissues.

In a fourth aspect, the present invention provides a kit for detecting colon cancer in a subject, comprising (1) a standard control that provides an average amount of VSTM2A protein or VSTM2A mRNA; and (2) an agent that specifically and quantitatively identifies VSTM2A protein or VSTM2A mRNA. In some cases, the agent may be an antibody that specifically binds the VSTM2A protein; or the agent may be a polynucleotide probe that hybridizes with the VSTM2A mRNA. For example, the polynucleotide probe hybridizes with at least a segment of SEQ ID NO:18 or 19 or a complement thereof. The agent may include a detectable moiety. In other cases, the kit may further comprise two oligonucleotide primers for specifically amplifying at least a segment of SEQ ID NO:18 or 19 or its complement in an amplification reaction. Typically, the kit will further include an instruction manual.

In a fifth aspect, the present invention provides a method for inhibiting growth of a colon cancer cell. The claimed method includes the step of contacting the colon cancer cell with (1) an effective amount of a polypeptide that comprises the amino acid sequence set forth in SEQ ID NO:26 or (2) a nucleic acid that comprises a polynucleotide sequence encoding SEQ ID NO:26. In some embodiments, the nucleic acid is an expression cassette comprising a promoter operably linked to the polynucleotide sequence encoding SEQ ID NO:26. Various promoters may be useful in this method, for example, the promoter may be an epithelium-specific promoter. In other embodiments, the nucleic acid comprises the polynucleotide sequence set forth in SEQ ID NO:18 or 19. In yet other embodiments, the colon cancer cell is within a patient's body.

In addition, the present invention provides a kit for detecting colon cancer. The kit comprises: (1) an agent that differentially modifies methylated and unmethylated DNA, and (2) an indicator that, after the agent has been used to treat a sample from a subject who is being tested for colon cancer, determines whether each CpG in a CpG-containing genomic sequence is methylated or unmethylated. The CpG-containing genomic sequence is at least a segment of SEQ ID NO:9 and comprises at least 1, 2, 3, 4, 5, or more CpG pairs. The present invention also provides a composition for inhibiting growth of a colon cancer cell. The composition contains an effective amount of (1) a polypeptide comprising the amino acid sequence set forth in SEQ ID NO:26 (e.g., a polypeptide consisting of the amino acid sequence of SEQ ID NO:26) or (2) a nucleic acid comprising or consisting of a polynucleotide sequence encoding SEQ ID NO:26 (e.g., a nucleic acid sequence comprising the polynucleotide sequence of SEQ ID NO:18 or 19), and a pharmaceutically acceptable carrier. In this regard, this invention further provides the use of a polypeptide comprising the amino acid sequence set forth in SEQ ID NO:26 (e.g., a polypeptide consisting of the amino acid sequence of SEQ ID NO:26) or a nucleic acid comprising a polynucleotide sequence encoding SEQ ID NO:18 or 19 (e.g., a nucleic acid sequence comprising or consisting of the polynucleotide sequence of SEQ ID NO:18 or 19) in preparing a medicament for inhibiting growth of a colon cancer cell.

DEFINITIONS

Figure 1:
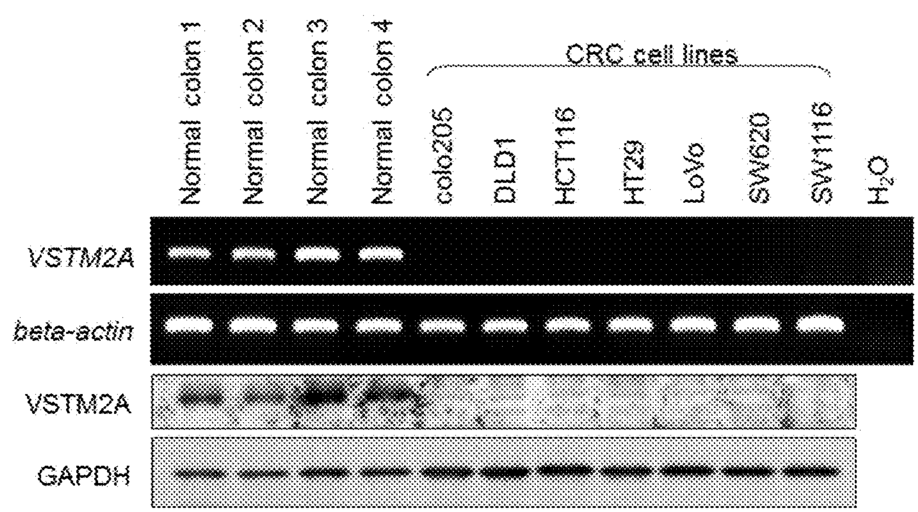
FIG. 1 shows VSTM2A mRNA and protein expression in normal tissues and colorectal cell lines in an embodiment.

The term "VSTM2A gene" or "VSTM2A protein," as used herein, refers to any naturally occurring variants or mutants, interspecies homologs or orthologs, or man-made variants of human VSTM2A gene or VSTM2A protein. The DNA sequence for a human wild-type VSTM2A mRNA is set forth in GenBank Accession No. NM_001301009 (provided herein as SEQ ID NO:19), which translate to a coding sequence (provided herein as SEQ ID NO:18) for a 240-amino acid VSTM2A protein (set forth in GenBank Accession No. NP_001287938, provided herein as SEQ ID NO:26). A VSTM2A protein within the meaning of this application typically has at least 80%, or 90%, or 95% or higher sequence identity to the human wild-type VSTM2A protein (e.g., SEQ ID NO:26).

In this disclosure the terms "colorectal cancer (CRC)" and "colon cancer" have the same meaning and refer to a cancer of the large intestine (colon), the lower part of human digestive system, although rectal cancer often more specifically refers to a cancer of the last several inches of the colon, the rectum. A "colorectal cancer cell" is a colon epithelial cell possessing characteristics of colon cancer and encompasses a precancerous cell, which is in the early stages of conversion to a cancer cell or which is predisposed for conversion to a cancer cell. Such cells may exhibit one or more phenotypic traits characteristic of the cancerous cells.

In this disclosure the term "or" is generally employed in its sense including "and/or" unless the content clearly dictates otherwise.

As used herein, the term "gene expression" is used to refer to the transcription of a DNA to form an RNA molecule encoding a particular protein (e.g., human VSTM2A protein) or the translation of a protein encoded by a polynucleotide sequence. In other words, both mRNA level and protein level encoded by a gene of interest (e.g., human VSTM2A gene) are encompassed by the term "gene expression level" in this disclosure.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, colon biopsy tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, stomach tissue, etc.) among other factors. Representative biopsy techniques include, but are not limited to, excisional biopsy, incisional biopsy, needle biopsy, surgical biopsy, and bone marrow biopsy and may comprise colonoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a variant VSTM2A protein used in the method of this invention (e.g., for treating colorectal cancer) has at least 80% sequence identity, preferably 85%, 90%, 91%, 92%, 93, 94%, 95%, 96%, 97%, 98%, 99%, or 100% identity, to a reference sequence, e.g., a wild-type human VSTM2A protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that reacts differentially with methylated and unmethylated DNA in a process through which distinguishable products or quantitatively distinguishable results (e.g. degree of binding or precipitation) are generated from methylated and non-methylated DNA, thereby allowing the identification of the DNA methylation status. Such processes may include, but are not limited to, chemical reactions (such as an unmethylated C U conversion by bisulfite), enzymatic treatment (such as cleavage by a methylation-dependent endonuclease), binding, and precipitation. Thus, an enzyme that preferentially cleaves methylated DNA is one capable of cleaving a DNA molecule at a much higher efficiency when the DNA is methylated, whereas an enzyme that preferentially cleaves unmethylated DNA exhibits a significantly higher efficiency when the DNA is not methylated. In the context of the present invention, a reagent that "differentially modifies" methylated and unmethylated DNA also refers to any reagent that exhibits differential ability in its binding to DNA sequences or precipitation of DNA sequences depending on their methylation status. One class of such reagents consists of methylated DNA binding proteins.

A "CpG-containing genomic sequence" as used herein refers to a segment of DNA sequence at a defined location in the genome of an individual. Typically, a "CpG-containing genomic sequence" is at least 15 contiguous nucleotides in length and contains at least one CpG pair. In some cases, it can be at least 18, 20, 25, 30, 50, 80, 100, 150, or 180 contiguous nucleotides in length and contains at least 2, 3, 4, 5, 6, 7, 8, 9, or 10 CpG pairs. For any one "CpG-containing genomic sequence" at a given location, e.g., within a region of the human VSTM2A genomic sequence (such as the region containing the promoter and exon 1, e.g., sequence segments shown in FIG. 2), nucleotide sequence variations may exist from individual to individual and from allele to allele even for the same individual. Furthermore, a "CpG-containing genomic sequence" may encompass a nucleotide sequence transcribed or not transcribed for protein production, and the nucleotide sequence can be a protein-coding sequence, a non protein-coding sequence (such as a transcription promoter), or a combination thereof.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce $F(ab)'_2$, a dimer of Fab which itself is a light chain joined to $V_H$-$C_H1$ by a disulfide bond. The $F(ab)'_2$ can be reduced under mild conditions to break the disulfide linkage in the hinge region thereby converting the $(Fab')_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established standard control (such as an average expression level of VSTM2A mRNA or VSTM2A protein found in non-cancerous colon tissue). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human VSTM2A or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1 of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

"Standard control" as used herein refers to a predetermined amount or concentration of a polynucleotide sequence or polypeptide, e.g., VSTM2A mRNA or protein, that is present in an established normal disease-free tissue sample, e.g., a normal colon epithelial tissue sample. The standard control value is suitable for the use of a method of the present invention, to serve as a basis for comparing the amount of VSTM2A mRNA or protein that is present in a test sample. An established sample serving as a standard control provides an average amount of VSTM2A mRNA or VSTM2A protein that is typical for a colon epithelial tissue sample (e.g., colon mucosa) of an average, healthy human without any colon disease especially colorectal cancer as conventionally defined. A standard control value may vary depending on the nature of the sample as well as other factors such as the gender, age, ethnicity of the subjects based on whom such a control value is established.

The term "average," as used in the context of describing a human who is healthy, free of any colon disease (especially colon cancer) as conventionally defined, refers to certain characteristics, especially the amount of human VSTM2A mRNA or protein, found in the person's colon tissue, e.g., epithelial tissue or colon mucosa, that are representative of a randomly selected group of healthy humans who are free of any colon diseases (especially colon cancer). This selected group should comprise a sufficient number of humans such that the average amount of VSTM2A mRNA or protein in the colon mucosa among these individuals reflects, with reasonable accuracy, the corresponding amount of VSTM2A mRNA/protein in the general population of healthy humans. In addition, the selected group of humans generally have a similar age to that of a subject whose colon tissue sample is tested for indication of colorectal cancer. Moreover, other factors such as gender, ethnicity, medical history are also considered and preferably closely matching between the profiles of the test subject and the selected group of individuals establishing the "average" value.

The term "amount" as used in this application refers to the quantity of a polynucleotide of interest or a polypeptide of interest, e.g., human VSTM2A mRNA or VSTM2A protein, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an polynucleotide encoding VSTM2A mRNA is the amount of said polynucleotide to achieve an increased level of VSTM2A protein expression or biological activity, such that the symptoms of colorectal cancer are reduced, reversed, eliminated, prevented, or delayed of the onset in a patient who has been given the polynucleotide for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, colorectal cancer. Subjects also include individuals currently undergoing therapy that seek manipulation of the therapeutic regimen. Subjects or individuals in need of treatment include those that demonstrate symptoms of colorectal cancer or are at risk of suffering from colorectal cancer or its symptoms. For example, a subject in need of treatment includes individuals with a genetic predisposition or family history for colorectal cancer, those that have suffered relevant symptoms in the past, those that have been exposed to a triggering substance or event, as well as those suffering from chronic or acute symptoms of the condition. A "subject in need of treatment" may be at any age of life.

"Inhibitors," "activators," and "modulators" of VSTM2A protein are used to refer to inhibitory, activating, or modulating molecules, respectively, identified using in vitro and in vivo assays for VSTM2A protein binding or signaling, e.g., ligands, agonists, antagonists, and their homologs and mimetics. The term "modulator" includes inhibitors and activators. Inhibitors are agents that, e.g., partially or totally block carbohydrate binding, decrease, prevent, delay activation, inactivate, desensitize, or down regulate the activity of VSTM2A protein. In some cases, the inhibitor directly or indirectly binds to VSTM2A protein, such as a neutralizing antibody. Inhibitors, as used herein, are synonymous with inactivators and antagonists. Activators are agents that, e.g., stimulate, increase, facilitate, enhance activation, sensitize or up regulate the activity of VSTM2A protein. Modulators include VSTM2A protein ligands or binding partners, including modifications of naturally-occurring ligands and synthetically-designed ligands, antibodies and antibody fragments, antagonists, agonists, small molecules including carbohydrate-containing molecules, siRNAs, RNA aptamers, and the like.

DETAILED DESCRIPTION OF THE INVENTION

I. Introduction colorectal cancer patients often face a grim prognosis due to the nature of this disease in its lacking of specific symptoms during its early development stages. Early detection of colorectal cancer is therefore critical for improving patient survival rate. Moreover, it is also of practical importance to predict the likelihood of mortality from colorectal cancer among patients who have already received a diagnosis of colorectal cancer for any time period after the initial diagnosis.

The present inventors discovered for the first time that expression of VSTM2A, both at the mRNA and protein levels, is suppressed in colorectal cancer cells. This suppressed expression of VSTM2A protein is due to increased methylation in the VSTM2A genomic sequence, especially in the promoter region of the gene, which leads to decreased transcription of VSTM2A mRNA. This discovery provides important means for detecting, monitoring, and treating colorectal cancer. Generally, a lower than normal VSTM2A mRNA/protein level seen in a test subject, who may or may not exhibit any signs of digestive tract-related disorder or condition, indicates a high likelihood that the subject already has or will later develop colorectal cancer. Similarly, a higher than normal level of methylation in the VSTM2A gene sequence, especially in the promoter region, indicates a high likelihood that the subject already has or will later develop colorectal cancer. Further, among colorectal cancer patients, individuals with lower level of VSTM2A expression in mRNA or protein or higher level of VSTM2A DNA methylation suffer a higher likelihood of mortality from colorectal cancer during a post-diagnosis time period in comparison with their counterparts who have a normal or higher level of VSTM2A expression in mRNA or protein or a normal or lower level of VSTM2A DNA methylation.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed.

2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human VSTM2A gene, and synthetic oligonucleotides (e.g., primers) can be verified using, e.g., the chain termination method for sequencing double-stranded templates of Wallace et al., *Gene* 16: 21-26 (1981).

III. Acquisition of Tissue Samples and Analysis of VSTM2A mRNA or DNA

The present invention relates to measuring the amount of VSTM2A mRNA or analyzing the methylation pattern of VSTM2A genomic DNA found in a person's colon tissue, especially colon epithelial sample, as a means to detect the presence, to assess the risk of developing, and/or to monitor the progression or treatment efficacy of colorectal cancer. Thus, the first steps of practicing this invention are to obtain a colon epithelial tissue sample from a test subject and extract mRNA or DNA from the sample.

A. Acquisition and Preparation of Colon Tissue Samples

A colon tissue sample is obtained from a person to be tested or monitored for colorectal cancer using a method of the present invention. Collection of colon epithelial tissue sample from an individual is performed in accordance with the standard protocol hospitals or clinics generally follow, such as during a colonoscopy. An appropriate amount of colon epithelium is collected and may be stored according to standard procedures prior to further preparation.

The analysis of VSTM2A mRNA or DNA found in a patient's colon epithelial sample according to the present invention may be performed using, e.g., colon mucosa. The methods for preparing tissue samples for nucleic acid extraction are well known among those of skill in the art. For example, a subject's colon mucosa sample should be first treated to disrupt cellular membrane so as to release nucleic acids contained within the cells.

B. Extraction and Quantitation of RNA

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of mRNA Level

Once mRNA is extracted from a sample, the amount of human VSTM2A mRNA may be quantified. The preferred method for determining the mRNA level is an amplification-based method, e.g., by polymerase chain reaction (PCR), especially reverse transcription-polymerase chain reaction (RT-PCR).

Prior to the amplification step, a DNA copy (cDNA) of the human VSTM2A mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of an mRNA species in a tissue sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA in a sample. For a review of branched-DNA signal amplification for direct quantitation of nucleic acid sequences in clinical samples, see Nolte, *Adv. Clin. Chem.* 33:201-235, 1998.

2. Other Quantitative Methods

The VSTM2A mRNA can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well-known techniques (see, e.g., Sambrook and Russell, supra), the presence of a band of the same size as the standard comparison is an indication of the presence of a target mRNA, the amount of which may then be compared to the control based on the intensity of the band. Alternatively, oligonucleotide probes specific to VSTM2A mRNA can be used to detect the presence of such mRNA species and indicate the amount of mRNA in comparison to the standard comparison, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^{3}H$, $^{125}I$, $^{35}S$, $^{14}C$, or $^{32}P$, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.,* 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.,* 255:137-149, 1983.

C. Detection of Methylation in VSTM2A Genomic Sequence

Methylation status of a segment of VSTM2A genomic sequence containing one or more CpG (cytosine-guanine dinucleotide) pairs is investigated to provide indication as to whether a test subject is suffering from colorectal cancer, whether the subject is at risk of developing colorectal cancer, or whether the subject's colorectal cancer is worsening or improving.

Typically a segment of the VSTM2A genomic sequence that includes the 5' untranslated region (such as the promoter region) and includes one or more CpG nucleotide pairs is analyzed for methylation pattern. For example, SEQ ID NO:17 or a portion thereof can be used to determine how many of the CpG pairs within the sequence are methylated and how many are not methylated. The sequence being analyzed should be long enough to contain at least 1 CpG dinucleotide pair and detection of methylation at this CpG site is typically adequate indication of the presence of colon cancer cells. The length of the sequence being analyzed is usually at least 15 or 20 contiguous nucleotides, and may be longer with at least 25, 30, 50, 75, 100, 150, 180, or up to 200 contiguous nucleotides. At least one, typically 2 or more, often 3, 4, 5, 6, 7, 8, 9, 10, 20, 25, 30, 50 or more, CpG nucleotide pairs are present within the sequence. In the cases of multiple (2 or more) CpG sites are analyzed for methylation status (which may be 100% methylated or at least 50% methylated), when at least 50% of the CpG pairs within the analyzed genomic sequence are shown to be methylated, subject being tested is deemed to have colon cancer or have an elevated risk of developing colon cancer. As an example, the 167-319 fragment of SEQ ID NO:17, which corresponds to the −117 to +36 segment shown in FIG. 2, a segment of VSTM2A genomic sequence (−117 to +36 in relation to the transcription start site), can be chosen as a target sequence for the analysis. Some or majority of the CpG pairs in this region are found to be methylated in established colon cancer cell lines and samples taken from colon cancer, whereas non-cancerous colon epithelial cells showed very few, if any at all, methylated CpG sites (see, e.g., FIG. 2). For example, the presence of colon cancer or an increased risk for later developing colon cancer is established when at least 90% (or at least 22 CpG sites) of the 25 CpG sites within the region are found to be at least 50% methylated or when at least 50% (or at least 12 CpG sites) of the 25 CpG sites are found to be 100% methylated. For the purpose of determining the methylation pattern of a VSTM2A genomic sequence, bisulfite treatment followed by DNA sequencing is particularly useful, since bisulfite converts an unmethylated cytosine (C) to a uracil (U) while leaving methylated cytosines unchanged, allowing immediate identification through a DNA sequencing process. Optionally, an amplification process such as PCR is included after the bisulfite conversion and before the DNA sequencing.

1. DNA Extraction and Treatment

Methods for extracting DNA from a biological sample are well known and routinely practiced in the art of molecular biology, see, e.g., Sambrook and Russell, supra. RNA contamination should be eliminated to avoid interference with DNA analysis. The DNA is then treated with a reagent capable of modifying DNA in a methylation differential manner, i.e., different and distinguishable chemical structures will result from a methylated cytosine (C) residue and an unmethylated C residue following the treatment. Typically, such a reagent reacts with the unmethylated C residue(s) in a DNA molecule and converts each unmethylated C residue to a uracil (U) residue, whereas the methylated C residues remain unchanged. This unmethylated C→U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., *Proc. Natl. Acad. Sci. USA* 93:9821-9826, 1996).

As a skilled artisan will recognize, any other reagents that are unnamed here but have the same property of chemically (or through any other mechanism) modifying methylated and unmethylated DNA differentially can be used for practicing the present invention. For instance, methylation-specific modification of DNA may also be accomplished by methylation-sensitive restriction enzymes, some of which typically cleave an unmethylated DNA fragment but not a methylated DNA fragment, while others (e.g., methylation-dependent endonuclease McrBC) cleave DNA containing methylated cytosines but not unmethylated DNA. In addition, a combination of chemical modification and restriction enzyme treatment, e.g., combined bisulfite restriction analysis (COBRA) (Xiong et al. 1997 *Nucleic Acids Res.* 25(12): 2532-2534), is useful for practicing the present invention. Other available methods for detecting DNA methylation include, for example, methylation-sensitive restriction endonucleases (MSREs) assay by either Southern blot or PCR analysis, methylation specific or methylation sensitive-PCR (MS-PCR), methylation-sensitive single nucleotide primer extension (Ms-SnuPE), high resolution melting (HRM) analysis, bisulifte sequencing, pyrosequencing, methylation-specific single-strand conformation analysis (MS-SSCA), methylation-specific denaturing gradient gel electrophoresis (MS-DGGE), methylation-specific melting curve analysis (MS-MCA), methylation-specific denaturing high-performance liquid chromatography (MS-DHPLC), methylation-specific microarray (MSO). These assays can be either PCR analysis, quantitative analysis with fluorescence labelling or Southern blot analysis. Exemplary methylation sensitive DNA cleaving reagent such as restriction enzymes include AatII, AciI, AclI, AgeI, AscI, Asp718, AvaI, BbrP1, BceAI, BmgBI, BsaAI, BsaHI, BsiEI, BsiWI, BsmBI, BspDI, BsrFI, BssHII, BstBI, BstUI, ClaI, EagI, EagI-HF™, FauI, FseI, FspI, HaeII, HgaI, HhaI, HinP1I, HpaII, Hpy99I, HpyCH4IV, KasI, MluI, NarI, NgoMIV, NotI, NotI-HF™, NruI, Nt.BsmAI, PaeR7I, PspXI, PvuI, RsrII, SacII, SalI, SalI-HF™, SfoI, SgrAI, SmaI, SnaBI or TspMI.

2. Optional Amplification and Sequence Analysis

Following the modification of DNA in a methylation-differential manner, the treated DNA is then subjected to sequence-based analysis, such that the methylation status of the VSTM2A genomic sequence may be determined. An amplification reaction is optional prior to the sequence analysis after methylation specific modification. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., C→U) in a polynucleotide sequence for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

IV. Quantitation of Polypeptides

A. Obtaining Samples

The first step of practicing the present invention is to obtain a sample of colon epithelium from a subject being tested, assessed, or monitored for colorectal cancer, the risk of developing colorectal cancer, or the severity/progression of the condition. Samples of the same type should be taken from both a control group (normal individuals not suffering from any colon disorder especially neoplasia) and a test group (subjects being tested for possible colon cancer, for example). Standard procedures routinely employed in hospitals or clinics are typically followed for this purpose, as stated in the previous section.

For the purpose of detecting the presence of colorectal cancer or assessing the risk of developing colorectal cancer in test subjects, individual patients' colon mucosa samples may be taken and the level of human VSTM2A protein may be measured and then compared to a standard control. If a decrease in the level of human VSTM2A protein is observed when compared to the control level, the test subject is deemed to have colorectal cancer or have an elevated risk of developing the condition. For the purpose of monitoring disease progression or assessing therapeutic effectiveness in colorectal cancer patients, individual patient's colon epithelial samples may be taken at different time points, such that the level of human VSTM2A protein can be measured to provide information indicating the state of disease. For instance, when a patient's VSTM2A protein level shows a general trend of increase over time, the patient is deemed to be improving in the severity of colorectal cancer or the therapy the patient has been receiving is deemed effective. A lack of change in a patient's VSTM2A protein level or a continuing trend of decrease on other hand would indicate a worsening of the condition and ineffectiveness of the therapy given to the patient. Generally, a lower VSTM2A protein level seen in a patient indicates a more severe form of the colorectal cancer the patient is suffering from and a worse prognosis of the disease, as manifested in shorter life expectancy, higher rate of metastasis, resistance to therapy etc. Among colorectal cancer patients, one who has a lower level of VSTM2A protein expression in the colon cancer sample than that found in a second colorectal cancer patient has a higher likelihood of mortality compared to the second patient for any defined time period, such as 1-5 years post-diagnosis.

B. Preparing Samples for VSTM2A Protein Detection

The colon tissue sample from a subject is suitable for the present invention and can be obtained by well-known methods and as described in the previous section. In certain applications of this invention, colon mucosa may be the preferred sample type.

C. Determining the Level of Human VSTM2A Protein

A protein of any particular identity, such as VSTM2A protein, can be detected using a variety of immunological assays. In some embodiments, a sandwich assay can be performed by capturing the polypeptide from a test sample with an antibody having specific binding affinity for the polypeptide. The polypeptide then can be detected with a labeled antibody having specific binding affinity for it. Such immunological assays can be carried out using microfluidic devices such as microarray protein chips. A protein of interest (e.g., human VSTM2A protein) can also be detected by gel electrophoresis (such as 2-dimensional gel electrophoresis) and western blot analysis using specific antibodies. Alternatively, standard immunohistochemical techniques can be used to detect a given protein (e.g., human VSTM2A protein), using the appropriate antibodies. Both monoclonal and polyclonal antibodies (including antibody fragment with desired binding specificity) can be used for specific detection of the polypeptide. Such antibodies and their binding fragments with specific binding affinity to a particular protein (e.g., human VSTM2A protein) can be generated by known techniques.

Other methods may also be employed for measuring the level of VSTM2A protein in practicing the present invention. For instance, a variety of methods have been developed based on the mass spectrometry technology to rapidly and accurately quantify target proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring SIM) mode, and the electrospray ionization (ESI) based QTOP mass spectrometer. See, e.g., Pan et al., *J Proteome Res.* 2009 February; 8(2):787-797.

V. Establishing a Standard Control

In order to establish a standard control for practicing the method of this invention, a group of healthy persons free of any colon disease (especially any form of tumor such as colorectal cancer) as conventionally defined is first selected. These individuals are within the appropriate parameters, if applicable, for the purpose of screening for and/or monitoring colon cancer using the methods of the present invention. Optionally, the individuals are of same gender, similar age, or similar ethnic background.

The healthy status of the selected individuals is confirmed by well established, routinely employed methods including but not limited to general physical examination of the individuals and general review of their medical history.

Furthermore, the selected group of healthy individuals must be of a reasonable size, such that the average amount/concentration of human VSTM2A mRNA or VSTM2A protein in the colon tissue sample obtained from the group can be reasonably regarded as representative of the normal or average level among the general population of healthy people. Preferably, the selected group comprises at least 10 human subjects.

Once an average value for the VSTM2A mRNA or protein is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, or ethnic background.

VI. Treatment and Prevention of Colorectal Cancer

By illustrating the correlation of suppressed expression of VSTM2A protein and colon cancer, the present invention further provides a means for treating patients suffering from colon cancer: by way of increasing VSTM2A protein expression or biological activity. As used herein, treatment of colon cancer encompasses reducing, reversing, lessening, or eliminating one or more of the symptoms of colon cancer, as well as preventing or delaying the onset of one or more of the relevant symptoms.

Upon detecting suppressed expression of VSTM2A at mRNA/protein level cue to increased methylation level of VSTM2A, especially at the promoter region (e.g., SEQ ID NO:100), one may establish the presence of colorectal cancer in a patient or an increased risk of later developing the disease in the patient. As a result of this determination, the patient may be subject to subsequent therapies or preventive/monitoring measures, especially those fitting certain profiles, such as those with a family history of colon cancer, such that the symptoms of these conditions may be prevented, eliminated, ameliorated, reduced in severity and/or frequency, or delayed in their onset. For example, a physician may prescribe both pharmacological and non-pharmacological treatments such as lifestyle modification (e.g., reduce body weight by 5% or more, assume a healthier life style including following a high fibre diet and maintaining a higher level of physical activities such as walking for at least 150 minutes weekly, and undergo routine screening/examination such as regular colonoscopy every 5 years). In some cases, when the presence of colorectal cancer is confirmed by way of other diagnostic means (e.g., colonoscopy), aggressive treatment may be used such as surgical intervention as well as radio- and/or chemo-therapy.

A. Increasing VSTM2A Expression or Activity

1. Nucleic Acids Encoding VSTM2A Proteins

Enhancement of VSTM2A gene expression can be achieved through the use of nucleic acids encoding a functional VSTM2A protein. Such nucleic acids can be single-stranded nucleic acids (such as mRNA) or double-stranded nucleic acids (such as DNA) that can translate into an active form of VSTM2A protein under favorable conditions.

In one embodiment, the VSTM2A-encoding nucleic acid is provided in the form of an expression cassette, typically recombinantly produced, having a promoter operably linked to the polynucleotide sequence encoding the VSTM2A protein. In some cases, the promoter is a universal promoter that directs gene expression in all or most tissue types; in other cases, the promoter is one that directs gene expression specifically in epithelial cells, especially in colon epithelium. Administration of such nucleic acids can increase the VSTM2A protein expression in the target tissue, e.g., colon epithelium. Since the human VSTM2A gene sequence encoding its mRNA is known as GenBank Accession No. NM_001301009 and provided herein as SEQ ID NO:19, and its cDNA sequence is provided herein as SEQ ID NO:18, one can derive a suitable VSTM2A-encoding nucleic acid from the sequence, species homologs, and variants of these sequences.

2. VSTM2A Proteins

By directly administering an effective amount of an active VSTM2A protein to a patient suffering from colorectal cancer and exhibiting suppressed VSTM2A protein expression or activity, the disease may also be effectively treated. For example, this can be achieved by administering a recombinantly produced VSTM2A protein possessing its biological activity to the patient suffering from colorectal cancer. Formulations and methods for delivering a protein- or polypeptide-based therapeutic agent are well known in the art.

3. Activators of VSTM2A Protein

Increased VSTM2A protein activity can be achieved with an agent that is capable of activating the expression of VSTM2A protein or enhancing the activity of VSTM2A protein. For example, a demethylating agent (e.g., 5-Aza) may be able to activate VSTM2A gene expression by removing the suppression of VSTM2A gene expression caused by methylation of the promoter region of this gene. Other activating agents may include transcriptional activators specific for the VSTM2A promoter and/or enhancer. Such activating agents can be screened for and identified using the VSTM2A expression assays described in the examples herein.

Agonists of the VSTM2A protein, such as an activating antibody, are another kind of activators of the VSTM2A protein. Such activators act by enhancing the biological activity of the VSTM2A protein, typically (but not necessarily) by direct binding with the VSTM2A protein and/or its interacting proteins. Preliminary screening for such agonists may start with a binding assay for identifying molecules that physically interact with VSTM2A protein.

B. Pharmaceutical Compositions

1. Formulations

Compounds of the present invention are useful in the manufacture of a pharmaceutical composition or a medicament. A pharmaceutical composition or medicament can be administered to a subject for the treatment of colorectal cancer.

Compounds used in the present invention, e.g., a VSTM2A protein, a nucleic acid encoding VSTM2A protein, or an activator of VSTM2A gene expression, are useful in the manufacture of a pharmaceutical composition or a medicament comprising an effective amount thereof in conjunction or mixture with excipients or carriers suitable for application.

An exemplary pharmaceutical composition for enhancing VSTM2A expression comprises (i) an express cassette comprising a polynucleotide sequence encoding a human VSTM2A protein as described herein, and (ii) a pharmaceutically acceptable excipient or carrier. The terms pharmaceutically-acceptable and physiologically-acceptable are used synonymously herein. The expression cassette may be provided in a therapeutically effective dose for use in a method for treatment as described herein.

A VSTM2A protein or a nucleic acid encoding a VSTM2A protein can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the inhibitor to be delivered is incorporated as part of a liposome, alone or in conjunction with a molecule which binds to, e.g., a receptor prevalent among the targeted cells (e.g., epithelial cells), or with other therapeutic or immunogenic compositions. Thus, liposomes filled with a desired inhibitor of the invention can be directed to the site of treatment, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) *Ann. Rev. Biophys. Bioeng.* 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

2. Routes of Administration

Suitable formulations for topical application, e.g., to the colon mucosa, are preferably aqueous solutions, ointments, creams or gels well-known in the art. Such may contain solubilizers, stabilizers, tonicity enhancing agents, buffers and preservatives.

Suitable formulations for transdermal application include an effective amount of a compound or agent of the present invention with carrier. Preferred carriers include absorbable pharmacologically acceptable solvents to assist passage through the skin or epithelium of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a VSTM2A protein or a nucleic acid encoding a VSTM2A protein, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds and agents of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the active ingredient, e.g., a VSTM2A protein or a nucleic acid encoding a VSTM2A protein, may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The therapeutic agent can also be formulated in rectal compositions, for example, suppositories or retention enemas, for example, containing conventional suppository bases, for example, cocoa butter or other glycerides.

Furthermore, the active ingredient can be formulated as a depot preparation. Such long-acting formulations can be administered by implantation (for example, subcutaneously or intramuscularly) or by intramuscular injection. Thus, for example, the active ingredient can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of a compound as described herein that increases the level or activity of VSTM2A protein, and (ii) another therapeutic agent. When used with a compound of the present invention, such therapeutic agent may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

3. Dosage

Pharmaceutical compositions or medicaments can be administered to a subject at a therapeutically effective dose to prevent, treat, or control colorectal cancer as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each type of VSTM2A protein or nucleic acid encoding a VSTM2A protein will likely have a unique dosage. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents may be administered for multiple days at the therapeutically effective daily dose. Thus, therapeutically effective administration of compounds to treat a pertinent condition or disease described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds or agents may vary depending on the relative potency of individual compounds or agents and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any agents used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Exemplary dosages for VSTM2A protein or a nucleic acid encoding a VSTM2A protein described herein are provided. Dosage for a VSTM2A-encoding nucleic acid, such as an expression cassette, can be between 0.1-0.5 mg/eye, with intravitreous administration (e.g., 5-30 mg/kg). Small organic compounds activators can be administered orally at between 5-1000 mg, or by intravenous infusion at between 10-500 mg/ml. Monoclonal antibody activators can be administered by intravenous injection or infusion at 50-500 mg/ml (over 120 minutes); 1-500 mg/kg (over 60 minutes); or 1-100 mg/kg (bolus) five times weekly. VSTM2A Protein or peptide activators can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical anti-inflammatories, pain relievers, anti-histamines, anesthetic compounds, and the like. The additional therapeutic compound can be administered at the same time as, or even in the same composition with, main active ingredient (e.g., a VSTM2A protein or a nucleic acid encoding the protein). The additional therapeutic compound can also be administered separately, in a separate composition, or a different dosage form from the main active ingredient. Some doses of the main ingredient, such as a VSTM2A protein or a nucleic acid encoding a VSTM2A protein, can be administered at the same time as the additional therapeutic compound, while others are administered separately, depending on the particular symptoms and characteristics of the individual.

The dosage of a pharmaceutical composition of the invention can be adjusted throughout treatment, depending on severity of symptoms, frequency of recurrence, and physiological response to the therapeutic regimen. Those of skill in the art commonly engage in such adjustments in therapeutic regimen.

VII. Kits and Devices

The invention provides compositions and kits for practicing the methods described herein to assess the level of VSTM2A mRNA or VSTM2A protein in a subject, which can be used for various purposes such as detecting or diagnosing the presence of colorectal cancer, determining the risk of developing colorectal cancer, and monitoring the progression of colorectal cancer in a patient, including assessing the likelihood of mortality from colorectal cancer.

Kits for carrying out assays for determining VSTM2A mRNA level typically include at least one oligonucleotide useful for specific hybridization with at least one segment of the VSTM2A coding sequence or its complementary sequence. Optionally, this oligonucleotide is labeled with a detectable moiety. In some cases, the kits may include at least two oligonucleotide primers that can be used in the amplification of at least one segment of VSTM2A DNA or mRNA by PCR, particularly by RT-PCR. Table 1 provides some examples of suitable primers.

Kits for carrying out assays for determining VSTM2A protein level typically include at least one antibody useful for specific binding to the VSTM2A protein amino acid sequence. Optionally, this antibody is labeled with a detectable moiety. The antibody can be either a monoclonal antibody or a polyclonal antibody. In some cases, the kits may include at least two different antibodies, one for specific binding to the VSTM2A protein (i.e., the primary antibody) and the other for detection of the primary antibody (i.e., the secondary antibody), which is often attached to a detectable moiety.

Typically, the kits also include an appropriate standard control. The standard controls indicate the average value of VSTM2A protein or mRNA in the colon epithelium of healthy subjects not suffering from colorectal cancer. In some cases such standard control may be provided in the form of a set value. In addition, the kits of this invention may provide instruction manuals to guide users in analyzing test samples and assessing the presence, risk, or state of colorectal cancer in a test subject.

In a further aspect, the present invention can also be embodied in a device or a system comprising one or more such devices, which is capable of carrying out all or some of the method steps described herein. For instance, in some cases, the device or system performs the following steps upon receiving a colon tissue sample, e.g., a colon mucosa sample taken from a subject being tested for detecting colorectal cancer, assessing the risk of developing colorectal cancer, or monitored for progression of the condition: (a) determining in sample the amount or concentration of VSTM2A mRNA, VSTM2A protein; (b) comparing the amount or concentration with a standard control value; and (c) providing an output indicating whether colorectal cancer is present in the subject or whether the subject is at risk of developing colorectal cancer, or whether there is a change, i.e., worsening or improvement, in the subject's colorectal cancer condition. In other cases, the device or system of the invention performs the task of steps (b) and (c), after step (a) has been performed and the amount or concentration from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Introduction

The current invention is based on the identification of the tumor suppressor gene VSTM2A and its role in colorectal cancer. Protein expression and promoter methylation of this VSTM2A can serve as new diagnostic markers as well as to provide prognostic information relating to the survival of colorectal cancer patients who have been diagnosed with the disease.

Colorectal cancer is a major cause of morbidity and mortality throughout the world. The prognosis of colorectal cancer patients is still poor, although improving surgical and adjuvant treatment approaches. 5-year overall survival from colorectal cancer is generally in the range 25-30%. There is accumulating evidence that aberrant DNA methylation is a hallmark of colorectal cancer. Identification of novel tumor suppressor genes repressed by DNA methylation will provide insights into the functional roles in colorectal carcinogenesis and will be useful in discovering potential biomarkers.

In a previous study using MeDIP-chip for a genome-wide screen for hypermethylated candidates in colorectal cancer, the gene forkhead box F2 (VSTM2A), an important transcription factor regulates tissue development, extracellular matrix synthesis, and epithelial-mesenchymal interactions, was identified to be preferentially methylated in colorectal cancer. Inactivation of VSTM2A by epigenetic mechanism may play a role during colorectal carcinogenesis.

The present inventors discovered that VSTM2A was down-regulated by promoter methylation in colorectal cancer cells, and VSTM2A was also down-regulated by promoter methylation in primary colorectal tumors. Restoration of VSTM2A expression inhibits cancer cell growth and induces programmed cell death mediated through inhibits Wnt signaling by directly promoting β-catenin degradation.

VSTM2A mRNA level was significantly reduced in 40 colorectal cancer specimens compared with adjacent normal by real-time PCR (P<0.05). VSTM2A proteins were significantly decreased in 14 randomly selected colorectal cancer samples compared with the normal counterpart by Western blot (P<0.01). Moreover, a negative association between VSTM2A promoter methylation and mRNA expression was demonstrated (spearman's rho=−0.37, P=14e-12). These results suggested that downregulation of VSTM2A was mediated by promoter methylation. The clinical application of VSTM2A methylation was further evaluated in 103 primary colorectal cancers patients. There was no correlation between the methylation status of VSTM2A and clinicopathologic features including age, gender, and TNM staging of colon cancer patients. Kaplan-Meier survival curves revealed that high VSTM2A methylation was negatively correlated with overall survival in a cohort of 103 colorectal cancer patients (P<0.05). Multivariate Cox regression analysis suggested that high VSTM2A methylation was an independent prognostic factor of poor survival of colorectal cancer patients (RR 1.93, 95% CI (1.15-3.21), P<0.05).

In brief, the tumor suppressive function of VSTM2A could potentially be applied to therapeutic intervention. Methylation status of VSTM2A closely relates to the survival of colorectal cancer patients especially in early stage and can be used as a new prognostic marker for colorectal cancer. Utilizing this information, individual who are deemed to have an increased likelihood of developing colorectal cancer (e.g., due to family history or environmental risk factors) could be screened regularly for early detection of the disease. Diagnosis of colorectal cancer at its earlier stages allows for patients a broader ranges of choices in terms of effective and appropriate therapeutic methods including but not limited to surgical intervention, chemotherapy, and radiotherapy, so as to improve patients' chances of long term survival from this deadly disease.

Materials and Methods

Human Colon Specimens

Tissue Samples 46 paired fresh primary colorectal cancer and adjacent non-tumor sites were obtained during operation from colorectal cancer patients diagnosed in the Prince of Wales Hospital of the Chinese University of Hong Kong. 29 paired fresh primary colorectal tumor and adjacent non-tumor sites from patients with colorectal cancer during operation were obtained at the Affiliated Hospital of Zhejiang University in Hangzhou, China. In addition, 158 paraffin embedded colorectal cancer tissue blocks and 19 paired paraffin embedded colorectal cancer and adjacent normal tissues were used for Immunohistochemistry analysis. All subjects provided informed consent for obtaining the study specimens. The study protocol was approved by the Clinical Research Ethics Committee of The Chinese University of Hong Kong, the Ethics Committee of the Zhejiang University.

Tumor Cell Line

Seven colorectal cancer cell lines (colo205, DLD1, HCT16, HT29, LoVo, SW620, and SW1116) and 293FT cell line were used in this study. Cell lines were maintained in RPMI-1640 or DMEM medium (Gibco BRL, Rockville, Md.) with 10% fetal bovine serum.

Gene Expression Analysis

RNA Isolation

Total RNA was isolated using Qiazol reagent (Qiagen, Valencia, Calif., USA). First, about 5-10×$10^6$ cells or 30 mg tissue was homogenized in 1 mL Qiazol reagent and incubated at room temperature for 10 min. For each sample, 0.2 mL chloroform was added. The mixture should be shaken vigorously for 15 sec and placed at room temperature for another 3 min. Samples were centrifuged at 12,000 g for 20 min at 4° C. and separated into two layers. The upper aqueous phase containing RNA was transferred to a new tube, mixed with 0.7 ml isopropanol, incubated at room temperature for 10 min and then centrifuged at 12,000 g for 10 min at 4° C. After discarding the supernatant, the RNA pellet was washed twice with 1 mL 75% ethanol; air dried for 5 min and re-dissolved the RNA with RNase-free $H_2O$. Contamination of DNA was eliminated by the RNase-free DNaseI digestion (GE Healthcare, Buckinghamshire, England). The quality and quantity of total RNA were determined by measuring absorbance at 260 nm/280 nm using NanoDrop ND-1000 (NanoDrop Technologies, Wilmington, Del., USA). The purified RNA was store at −80° C. until using.

cDNA Synthesis

MultiScribe Reverse Transcriptase Kit (Applied Biosystems, Foster City, Calif., USA) was used to synthesize cDNA. The reaction mixture contained 1× Reverse Transcriptase buffer, 1× dNTP, 1× random primer (supplied by kit), 2.5 U/μL reverse transcriptase, 1 U/μL RNase inhibitor and 2 μg total RNA. The mixture was incubated at 25° C. for 10 min, then 37° C. for 120 min, then 85° C. 5 min to inactivate the enzymes. The cDNA was stored at −80° C. until other application.

Semi-Quantitative PCR

Semi-quantitative PCR was performed in a total volume of 20 μL reaction containing GeneAmp 1×PCR Buffer II (Applied Biosystems), 2.5 mM $MgCl_2$, 200 μM each of dNTP, 200 nM each of primers, 0.4 U of AmpliTaq Gold DNA polymerase (Applied Biosystems) and 30~50 ng cDNA. The PCR program started with an initial denaturation at 94° C. for 10 min, followed by 32-35 cycles (94° C. for 30 sec, annealing temperature for 30 sec, and 72° C. for 30 sec) of amplification, with a final extension at 72° C. for 10 min. The PCR bands were visualized under ultraviolet light and photographed. The expression of the target gene was normalized by the expression of housekeeping gene β-actin, which served as an internal control. All primers used to amplify the transcripts are listed in Table 1.

DNA Methylation Analysis

Genomic DNA Extraction

Genomic DNA from GC cell lines and tissue samples were isolated by using DNA mini kit (Qiagen) according to the kit protocol. About 25 mg samples were lysed in 180 μL of QIAamp ATL buffer and 20 μL of proteinase K in a 1.5 mL microcentrifuge tubes for 1 hour at 56° C. Four microliter of RNase A (100 mg/ml, QIAgen) was added and mixed by pulse-vortexing for 15 s followed by 2 min incubation at room temperature. Then 200 μL of AL buffer was added to the lysate and samples were incubated for 10 min at 70° C. After adding 200 μL of absolute ethanol, the solution was mixed by pulse-vortexing for 15 s. Then lysates were purified over a QIAamp column as specified by the manufacturer. The genomic DNA was diluted in 200 μL DNase-free $H_2O$. The quality and quantity of DNA were determined by measuring absorbance at 260 nm/280 nm using NanoDrop ND-1000 (NanoDrop).

Sodium Bisulfite Conversion

Five μg genomic DNA in 30 μL TE buffer (Sigma-Aldrich) was mixed with 3.3 μL of 3 mM NaOH to a final concentration of 0.3 mM and incubate at 37° C. for 15 min. Denatured DNA was mixed with 333 μL of bisulfite solution and treated in darkness for 4 hr at 55° C. The bisulfite solution was prepared as 2.4 M sodium metabisulfite (pH 5.0-5.2) (Sigma-Aldrich) and 0.5 mM hydroquinone (Sigma-Aldrich). The treated DNA was desalted and purified using the Qiaex II kit (Qiagen) according to the protocol supplied by the kit. DNA was then treated with 0.3 M NaOH at 37° C. for 15 min and precipitated with 3 M ammonium acetate and 3 volumes of ethanol. Recovered DNA was dissolved in 100 μL TE buffer (pH 8.0) and stored at −20° C.

Demethylation Treatment Using 5-Aza-2'-Deoxycytidine (5-Aza)

Cells were seeded at a density of $1\times10^5$/100-mm dishes and grew for 24 hr. Cells were then treated with 2 μM 5-Aza (Sigma-Aldrich) for 5 days. The 5-Aza was replenished every day. The gene expression of VSTM2A was evaluated using semi-quantitative PCR.

Direct Bisulfite Genomic Sequencing (BGS)

Bisulfite treated DNA was amplified with primers listed in Table 1. PCR amplification with 2 μL of bisulfite-treated DNA gives a PCR product of 201 bp, containing 10 CpG dinucleotides at the VSTM2A promoter region. Amplified BGS products were sequenced. Sequencing analysis was performed by SeqScape software (Applied Biosystems, Foster City, Calif.).

Biological Function Analysis

Cloning of VSTM2A and Construction of Expression Vector

The full-length cDNA of VSTM2A gene expression vector was generated by PCR-cloning. Total RNA from human colorectal (Stratagene, La Jolla, Calif.) was reverse transcribed into cDNA. Sequence corresponding to the open reading frame (ORF) of VSTM2A was amplified by PCR. PCR product was cloned into the pcDNA3.1 expression vector.

VSTM2A Gene Transfection

Cells were seeded at ~$5\times10^6$ cells on a 10-cm dish without antibiotics for about 12 hr till the cell density reached about 80% confluent. Cells were then transfected with 8 μg VSTM2A and control vector (pCDNA3.1) respectively using FuGENE HD (promega) (24 μL) diluted in 1000 μL Opti-MEM (Invitrogen). After 24-48 hr incubation at 37° C. in a 5% $CO_2$ incubator, cells were harvested for testing of transgenic expression. For stable cell lines, cells were passaged at a 1:4 ratio into fresh growth medium with proper concentration of neomycin (G418) (Invitrogen). Stable transfection cells were harvested after 7-14 days of selection for functional assays.

Cell Viability Assay

Cell viability was determined by the 3-(4,5-dimethylthiazol-2-yl)-5-(3-carboxyme-thoxyphenyl)-2-(4-sulfophenyl)-2H-tetrazolium (MTS) assay (Promega, Madison, Wis.).

Colony Formation Assay

Two days after transfection, cells were subsequently split at 1:20 ratio on six-well plates with RPMI1640 in 10% FBS containing 500 μg/mL neomycin (G418). After 14-18 days of selection, cells were fixed with 70% ethanol for 10 min and stained with 0.5% crystal violet solution for 10 min. Colony with more than 50 cells per colony was counted. The experiment was conducted in three independent triplicates.

Propidium Iodide Cell Cycle Assay

The stably transfected HCT116, HT29 and DLD1 cells with pVSTM2A-Flag tag expressing or pcDNA3.1 empty vector were fixed in 70% ethanol and stained with 50 mg/ml propidium iodide (BD Pharmingen, San Jose, Calif.). The cells were then sorted by FACSCalibur (BD Biosciences, Franklin Lakes, N.J.) and cell cycle profiles were analyzed by ModFit 3.0 software (Verity Software House, Topsham, Me.).

Annexin V Apoptosis Assay

Annexin V is a protein which could bind the cell membrane after apoptosis have occurred and before membrane integrity has been lost. The proportion of apoptotic cells was evaluated using Annexin V and 7-amino-actinomycin (7-AAD) double staining. Briefly, the cells washed with 1×PBS was resuspended in 100 μL ice-cold annexin-binding buffer (10 mM HEPES, 140 mM NaCl and 2.5 mM CaCl2, pH 7.4) containing 5 μL Annexin V conjugated with Allophycocyanin (APC) and 2 μL 7-AAD staining (BD Biosciences). After incubation for 15 min at room temperature, cells were mixed with additional 400 μL of ice-cold annexin-binding buffer and analyzed using flow cytometry.

In Vivo Tumorigenicity Models

Stable VSTM2A expressing or control HCT116 cells ($1\times10^7$ cells in 0.1 ml phosphate-buffered saline) were injected subcutaneously into the right dorsal flank of four 4-week-old male Balb/c nude mice, separately (5/group). Tumor diameter was measured every 2 days. Tumor volume ($mm^3$) was estimated by measuring the longest and shortest diameter of the tumor and calculating as follows: volume=(shortest diameter)×(longest diameter)×0.5. After 18 days, the mice were sacrificed, and the tumors were weighed and fixed in formalin for histological analysis. All experimental procedures were approved by the Animal Ethics Committee of the Chinese University of Hong Kong.

Statistical Analysis

Data are expressed as mean±standard deviation (SD). The independent Student t test was used to compare the difference between two groups. One-way analysis of variance (ANOVA) was used to compare the difference between multiple groups. Correlation analysis was used to measure the strength of association between VSTM2A methylation and expression. Univariate and multivariate Cox regression analysis was performed to assess the prognostic value of VSTM2A protein level. Overall survival in relation to VSTM2A methylation status and protein expression was evaluated by Kaplan-Meier survival curve and log-rank test. Differences with $P\text{-value}<0.05$ were considered to be statistically significant.

Detailed Technical Description

Suppressing Tumor Growth by Exogenous VSTM2A Gene Expression in Colorectal Cancer; Cloning of VSTM2A and Construction of Expression Vector The full-length cDNA of VSTM2A gene expression vector was generated by PCR-cloning. Total RNA from human colorectal (Stratagene, La Jolla, Calif.) was reverse transcribed into cDNA. Sequence corresponding to the open reading frame (ORF) of VSTM2A was amplified by PCR. PCR product was cloned into the pcDNA3.1 expression vector. Cells were seeded at ~$5\times10^6$ cells on a 10-cm dish without antibiotics for about 12 hr till the cell density reached about 80% confluent. Cells were then transfected with 8 μg VSTM2A and control vector (pCDNA3.1) respectively using FuGENE HD (promega) (24 μL) diluted in 1000 μL Opti-MEM (Invitrogen). After 24~48 hr incubation at 37° C. in a 5% $CO_2$ incubator, cells were harvested for testing of transgenic expression. For stable cell lines, cells were passaged at a 1:4 ratio into fresh growth medium with proper concentration of neomycin (G418) (Invitrogen). Stable transfection cells were harvested after 7-14 days of selection for functional assays.

Colony Formation Assay

Two days after transfection, cells were subsequently split at 1:20 ratio on six-well plates with RPMI1640 in 10% FBS containing 500 μg/mL neomycin (G418). After 14-18 days of selection, cells were fixed with 70% ethanol for 10 min and stained with 0.5% crystal violet solution for 10 min. Colony with more than 50 cells per colony was counted. The experiment was conducted in three independent triplicates.

Cell Viability Assay

Cell viability was determined by the 3-(4,5-dimethylthiazol-2-yl)-5-(3-carboxyme-thoxyphenyl)-2-(4-sulfophenyl)-2H-tetrazolium (MTS) assay (Promega, Madison, Wis.).

All experiments were conducted three times in triplicates. Results were shown as the means±SD.

Flow Cytometry

For cell cycle analysis, The stably transfected HCT116, HT29 and DLD1 cells with pVSTM2A-Flag tag expressing or pcDNA3.1 empty vector were fixed in 70% ethanol and stained with 50 mg/ml propidium iodide (BD Pharmingen, San Jose, Calif.). The cells were then sorted by FACSCalibur (BD Biosciences, Franklin Lakes, N.J.) and cell cycle profiles were analyzed by ModFit 3.0 software (Verity Software House, Topsham, Me.). All experiments were conducted three times in triplicates.

The proportion of apoptotic cells was evaluated using Annexin V and 7-amino-actinomycin (7-AAD) double staining. Briefly, the cells washed with 1×PBS was resuspended in 100 μL ice-cold annexin-binding buffer (10 mM HEPES, 140 mM NaCl and 2.5 mM CaCl2, pH 7.4) containing 5 μL Annexin V conjugated with Allophycocyanin (APC) and 2 μL 7-AAD staining (BD Biosciences). After incubation for 15 min at room temperature, cells were mixed with additional 400 μL of ice-cold annexin-binding buffer and analyzed using flow cytometry.

In Vivo Tumorigenicity

Stable VSTM2A expressing or control HCT116 cells ($1\times10^7$ cells in 0.1 ml phosphate-buffered saline) were injected subcutaneously into the right dorsal flank of four 4-week-old male Balb/c nude mice, separately (5/group). Tumor diameter was measured every 2 days. Tumor volume ($mm^3$) was estimated by measuring the longest and shortest diameter of the tumor and calculating as follows: volume=(shortest diameter)$^2$×(longest diameter)×0.5. After 18 days, the mice were sacrificed, and the tumors were weighed and fixed in formalin for histological analysis. All experimental procedures were approved by the Animal Ethics Committee of the Chinese University of Hong Kong.

Gene Differentially Methylated in Colon Cancerous Tissues

Sodium Bisulfite Conversion

Five μg genomic DNA in 30 μL TE buffer (Sigma-Aldrich) was mixed with 3.3 μL of 3 mM NaOH to a final concentration of 0.3 mM and incubate at 37° C. for 15 min. Denatured DNA was mixed with 333 μL of bisulfite solution and treated in darkness for 4 hr at 55° C. The bisulfite solution was prepared as 2.4 M sodium metabisulfite (pH 5.0-5.2) (Sigma-Aldrich) and 0.5 mM hydroquinone (Sigma-Aldrich). The treated DNA was desalted and purified using the Qiaex II kit (Qiagen) according to the protocol supplied by the kit. DNA was then treated with 0.3 M NaOH at 37° C. for 15 min and precipitated with 3 M ammonium acetate and 3 volumes of ethanol. Recovered DNA was dissolved in 100 μL TE buffer (pH 8.0) and stored at −20° C.

Bisulfite Genomic Sequencing

In this assay, 2 μL bisulfite-treated DNA was amplified by primers of BGS. The primer sequences are forward 5'-TGTTTTTTAGAAGGGAGATTTTAG-3' SEQ ID NO: 15 and reverse 5'-TACCTAACTACCTACTTTCAACTACCTAAC-3' SEQ ID NO: 16. PCR amplification with 2 μL of bisulfate-treated DNA gives a PCR product of 201 bp, containing 10 CpG dinucleotides at the VSTM2A promoter region. Amplified BGS products were sequenced. Sequencing analysis was performed by SeqScape software (Applied Biosystems, Foster City, Calif.). Methylation percentage of each CpG site was calculated according this formula: Methylation %=$H_C/(H_C+H_T)\times100\%$, ($H_C$=Height of peak C, $H_T$=Height of peak T).

Evaluation of Protein Level of VSTM2A in Colon Tissues

Immunohistochemistry Analysis

Immunohistochemistry was performed on 5 μm-thick sections. After de-waxing and subsequently antigen retrieval, slides was incubated with primary antibody at 4° C. overnight and chromogen development will be performed using the EnVision system (DAKO).

Results

Silence or Down-Regulation of VSTM2A in Colorectal Cancer

VSTM2A is Epigenetically Suppressed in Cancer Cell Lines

Figure 2:
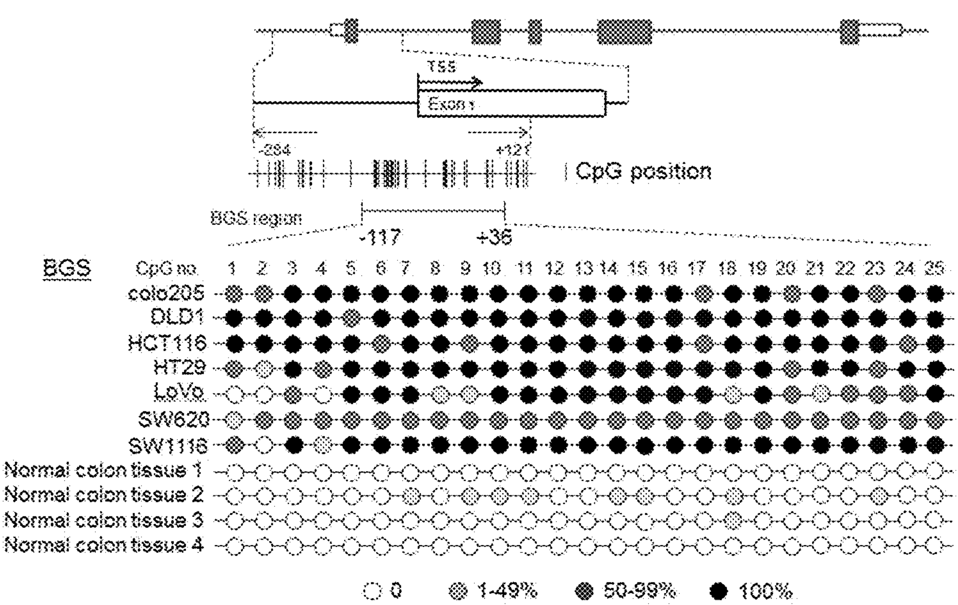
FIG. 2 shows bisulfate genomic sequencing result of VSTM2A promoter in colorectal cancer cell lines in an embodiment.

The mRNA expression of VSTM2A was silenced or reduced in all 7 examined colorectal cancer cell lines (FIG. 1). To elucidate the role of promoter methylation in the down-regulation of VSTM2A, VSTM2A methylation status was examined by BGS. Full or partial methylation was detected in colo205, DLD1, HCT16, HT29, LoVo, SW620, and SW1116. No methylation was detected in normal colon tissue (FIG. 2).

VSTM2A Expression is Restored after Demethylation Treatment

Figure 3:
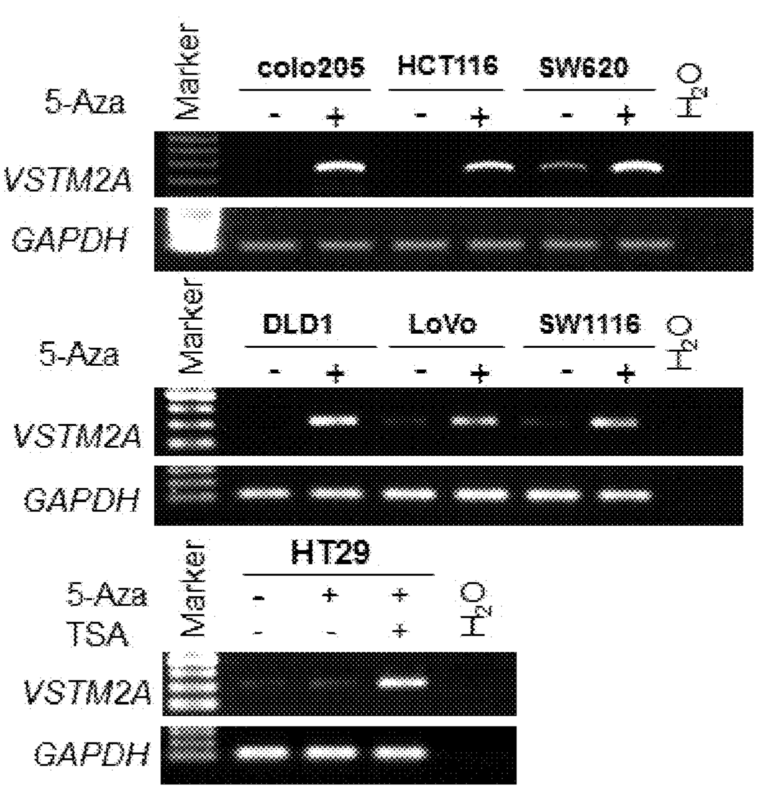
FIG. 3 shows the effect of a demethylating agent on VSTM2A expression in an embodiment.

To test whether methylation directly mediates VSTM2A silencing, we treated 7 silenced cell lines (colo205, DLD1, HCT16, HT29, LoVo, SW620, and SW1116) with demethylation agent 5-Aza. This treatment restored VSTM2A expression in colo205, DLD1, HCT16, LoVo, SW620, and SW1116 cell lines (FIG. 3). Although the restoration of VSTM2A by 5-Aza was insufficient in HT29, combination treatment with 5-Aza and histone deacetylase inhibitor TSA markedly restored VSTM2A expression (FIG. 3). These data suggested that transcriptional silence of VSTM2A was mainly mediated by promoter methylation in colorectal cancer cells.

Functional Assay

Ectopic Expression of VSTM2A Suppressed Colorectal Cancer Cell Growth

Figure 4:
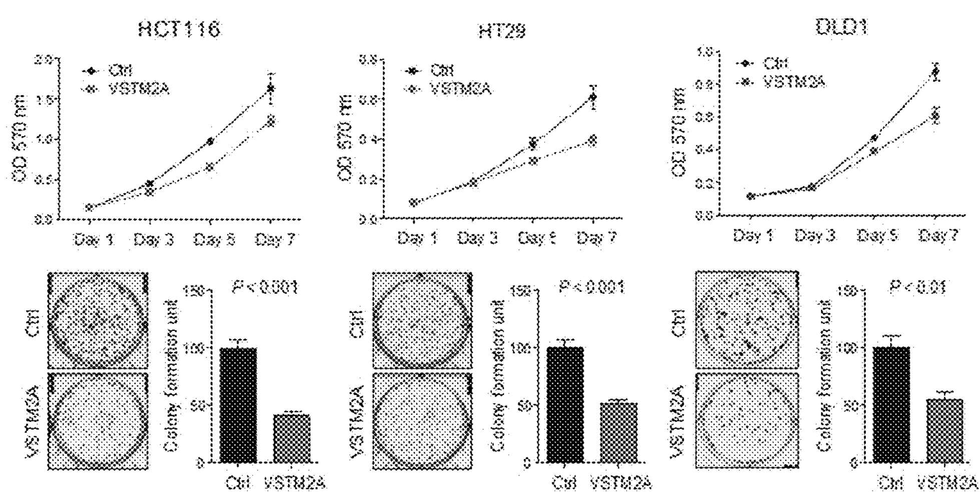
FIG. 4 shows the effect of VSTM2A expression on transfected cells in cell growth curve and colony formation assay in an embodiment.

In vitro biological effects of VSTM2A on cell growth in the VSTM2A non-expressing cell lines (HCT116, HT29 and DLD1) were examined by cell growth curve and colony formation assay. Ectopic expression of VSTM2A significantly inhibited cell viability in HCT116 (P<0.01), HT29 (P<0.01) and DLD1 (P<0.01) (FIG. 4). The colony numbers of VSTM2A-transfected cells were significantly decreased to 41% HCT116 (P<0.01), 51.3% in HT29 (P<0.01) and 55% in DLD1 (P<0.01) by colony formation assay compared with empty pcDNA3.1-transfected cells (FIG. 4).

Ectopic Expression of VSTM2A Arrests Cell Cycle at G2/M Phase

Figure 5:
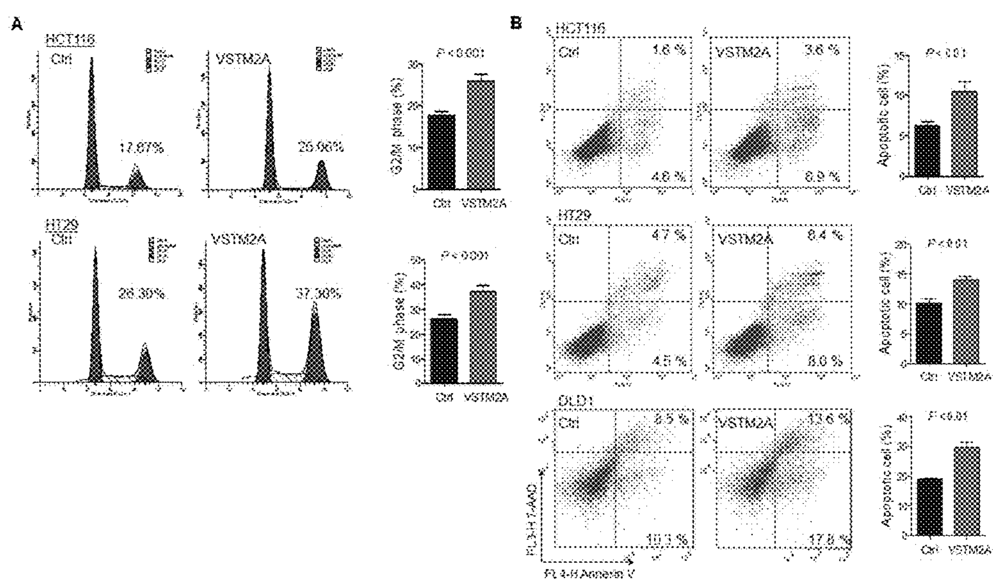
FIG. 5 shows ectopic expression of VSTM2A induced cell apoptosis, caused cell cycle arrest at G2/M phase in an embodiment.
Figure 6:
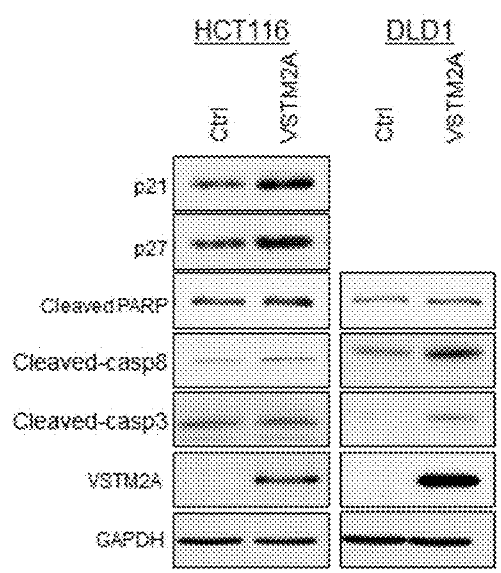
FIG. 6 shows cell apoptosis and cell cycle arrest marker protein induced by VSTM2A overexpression in an embodiment.

To determine the molecular mechanism by which VSTM2A suppresses cell growth, we investigated the effect of VSTM2A on cell cycle distribution by flow cytometry after propidium iodide staining. Ectopic expression of VSTM2A led to a significant increase in the number of the G2/M-phase cells of HCT116 (P<0.001) and HT29 (P<0.001) (FIG. 5A). Effect of VSTM2A overexpression on expression levels of candidates in cell cycle checkpoint signaling and apoptosis signaling pathway was validated by Western blotting. Overexpression of VSTM2A enhanced protein expression of p27, p21 (FIG. 6). These data confirmed the inhibitory effect of VSTM2A gene on cell proliferation.

Induction of Cell Apoptosis by VSTM2A

Suppression of cell growth in tumor cells is usually associated with concomitant activation of cell death pathways. We therefore examined the contribution of apoptosis to the observed growth inhibition of VSTM2A-transfected cells using flow cytometry with Annexin V and 7-AAD double staining. Our results showed an increase in the numbers of apoptotic cells (10.5±1.2% vs. 6.2±0.6%, P<0.01) in VSTM2A-transfected HCT116 cells compared with HCT116 cells transfected with control vector (FIG. 5B). This effect was also observed in VSTM2A-transfected HT29 cells (apoptotic cells 14.0±0.6% vs. 10.1±0.8%, P<0.01) and DLD1 cells (apoptotic cells 29.8±1.8% vs. 19.0±0.3%, P<0.01) being significantly increased compared with the control vector-transfected cells (FIG. 5B). Consistent with this finding, overexpression of VSTM2A enhanced protein expression of cleaved-caspase 3, cleaved-caspase 8, and cleaved PARP in HCT116 and DLD1 (FIG. 6). These findings suggested that apoptosis in conjunction with cell cycle arrest, as induced by VSTM2A, accounts for the growth inhibition in VSTM2A-expressing tumor cells.

VSTM2A Inhibits Tumor Growth in Nude Mice of Subcutaneous Xenograft Model

Figure 7:
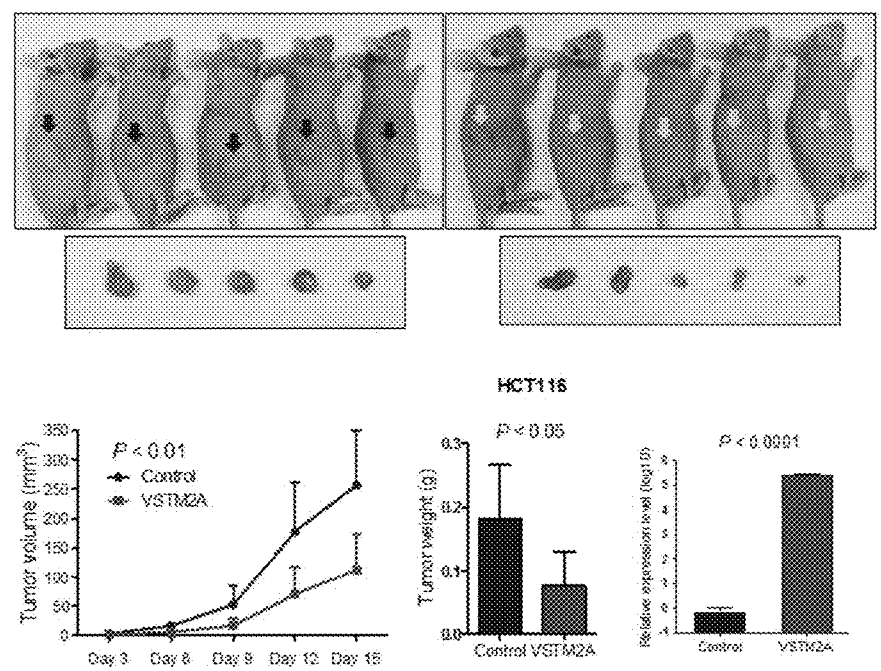
FIG. 7 shows VSTM2A inhibits tumor growth in nude mice of subcutaneous xenograft model in an embodiment.

To confirm the tumor suppressive effect of VSTM2A in colorectal cancer, we tested whether VSTM2A could suppress the growth of colorectal cancer cells in nude mice in vivo. The subcutaneous tumor growth curve of HCT116 stably transfected with VSTM2A or control vector in vivo is shown in FIG. 7. The tumor growth rates in the nude mice injected with the HCT116-VSTM2A cells were significantly slower than in those injected with the HCT116-vector control cells (FIG. 7). Fifteen days after injection, the mice were sacrificed and the xenografts were excised. The tumor volume was significantly lower in VSTM2A transfected nude mice as compared to the vector control mice (P<0.01, FIG. 7). The average tumor weight in the nude mice injected with HCT116-VSTM2A (0.076±0.054 g) was significantly lower compared with that in the control mice (0.182±0.084 g) (P<0.05, FIG. 7). The VSTM2A expression in the tumors was confirmed by quantitative real-time PCR and western blot, respectively (FIG. 7). The results from the in vivo model provide further evidence of the tumor-suppressive role of VSTM2A.

Methylation Status in Colorectal Cancer

VSTM2A Expression is Downregulated in Primary Colorectal Cancer Tissues

Figure 8:
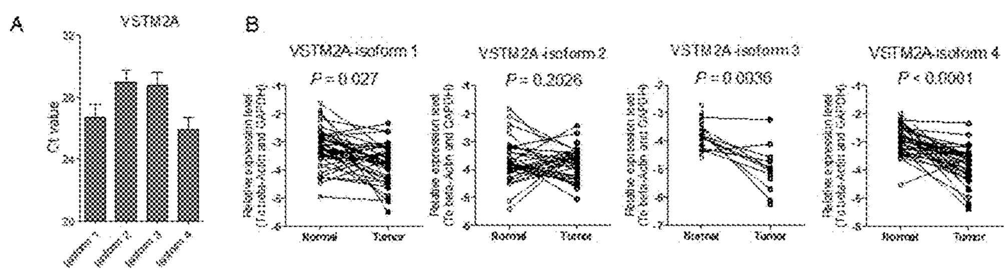
FIG. 8 shows four VSTM2A isoforms expression in CRC and adjacent normal tissue in an embodiment.
Figure 9:
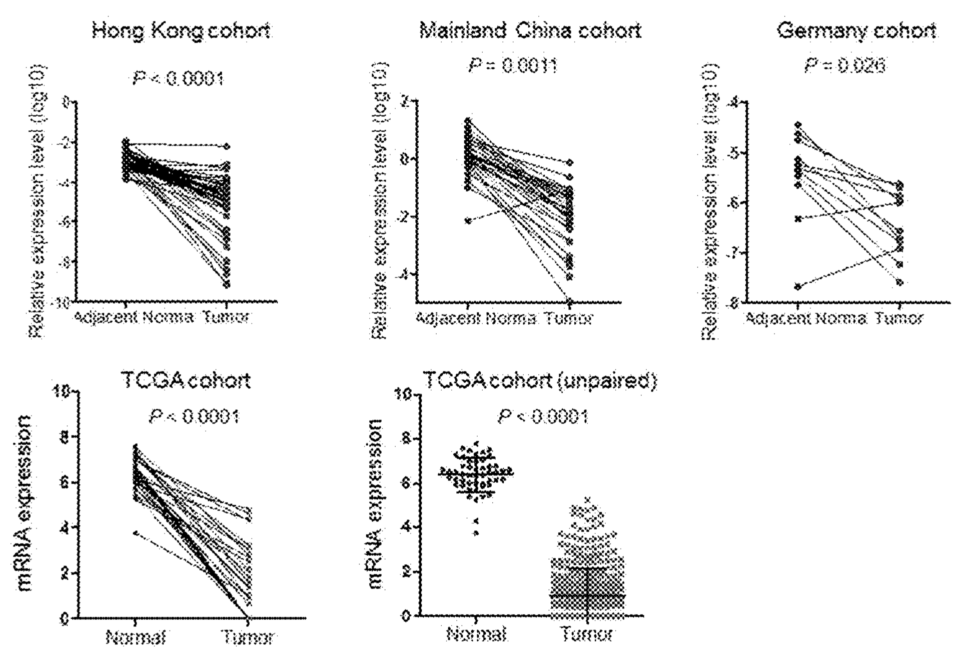
FIG. 9 shows VSTM2A mRNA expression is downregulated in primary colorectal cancer tissues in an embodiment.
Figure 10:
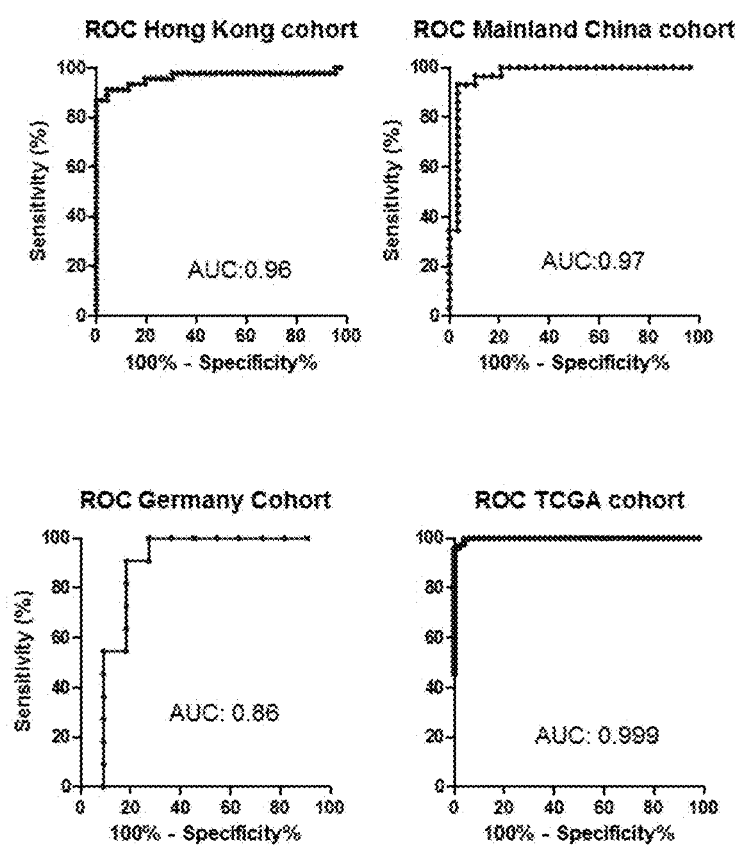
FIG. 10 shows the receiver operating characteristic (ROC curve) of VSTM2A mRNA expression in primary colorectal cancer tissues in an embodiment.
Figure 11:
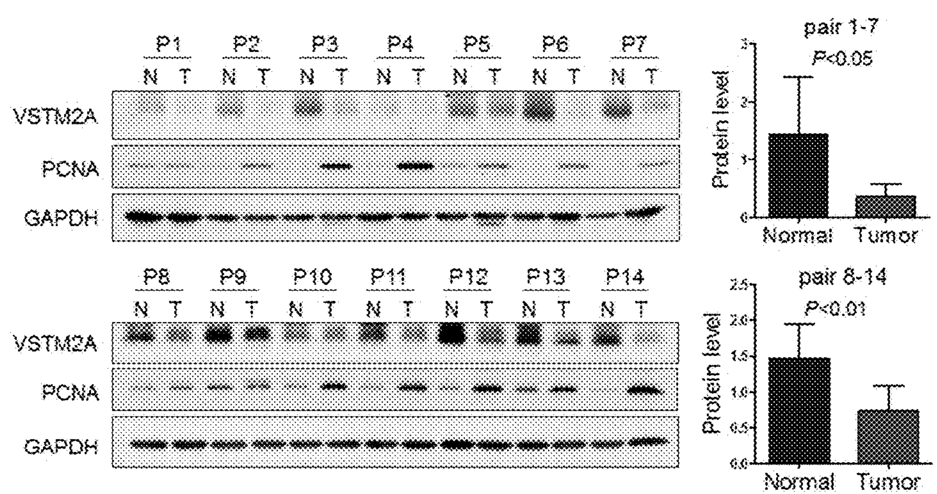
FIG. 11 shows VSTM2A protein expression is downregulated in primary colorectal cancer tissues and adjacent normal in an embodiment.
Figure 12:
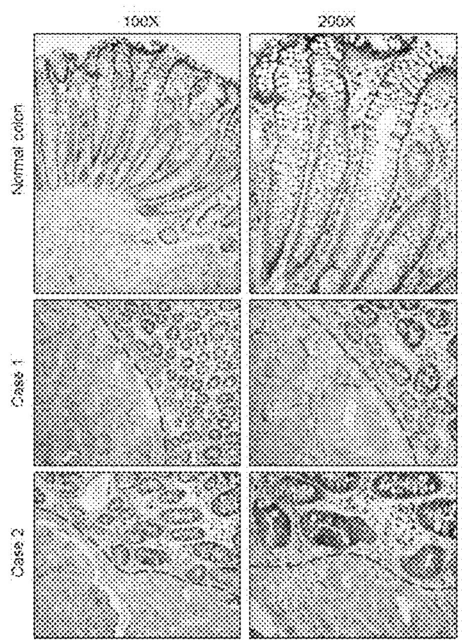
FIG. 12 shows immunohistochemistry staining of VSTM2A protein in primary colorectal cancer tissues and adjacent normal in an embodiment.
Figure 12:
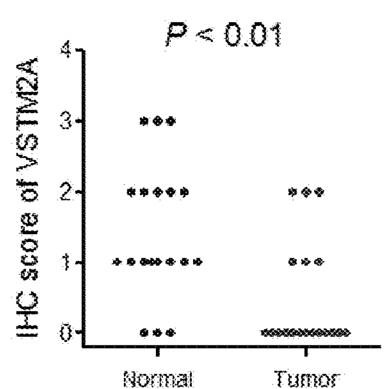
Figure 13:
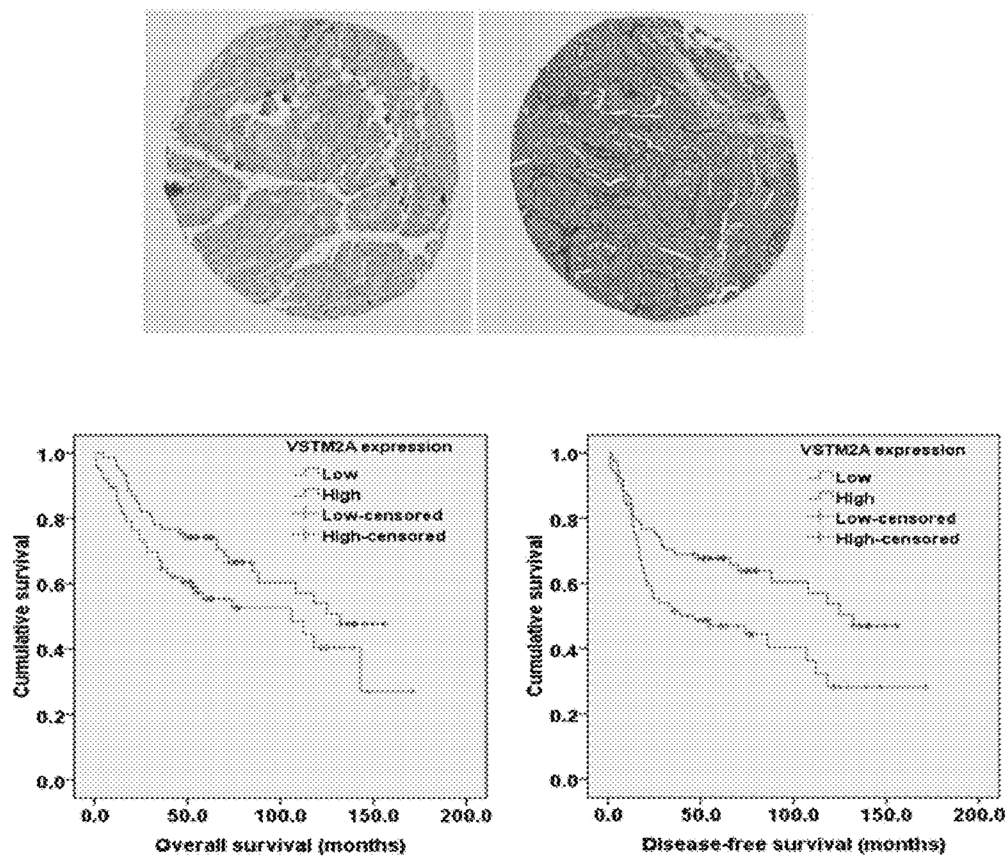
FIG. 13 shows high VSTM2A protein correlated with good disease-free survival and overall survival in patients with colorectal cancer in an embodiment.

Human VSTM2A has four transcripts that can generate protein products (http://www.ensembl.org). The four protein isoforms share an identical immunoglobulin V-set domain but show a different protein sequence at the C terminal. Among these isoforms, VSTM2A isoform 4 (NM_001301009) showed the highest expression level in normal mucosal specimens, suggesting a dominant role in normal colon tissues (FIG. 8A). Moreover, VSTM2A isoform 4 was reduced significantly in CRC (FIG. 8B). The mRNA level of VSTM2A isoform 4 were significantly downregulated in 86 colorectal cancers compared with adjacent normal tissues from 3 independent cohorts by quantitative real-time PCR (P<0.05; FIG. 9). To further confirm our findings, we analyzed the mRNA of VSTM2A in 416 CRC cases from TCGA database (https://genome-cancer.ucsc.edu/proj/site/hgHeatmap/). VSTM2A was dramatically increased in 32 cancer tissue compared with the paired adjacent normal tissues (P<0.0001) (FIG. 9). A similar trend was observed in unpaired CRC (n=380) and adjacent normal (n=50) samples from TCGA cohort (P<0.0001). The AUC for VSTM2A in the four cohorts ranges from 0.86-0.999 (FIG. 10). VSTM2A proteins were found to be significantly decreased in 13 out of 14 cancer tissue samples (93%) compared with the normal counterpart by western blot (FIG. 11). Immunohistochemistry (IHC) analysis with anti-VSTM2A antibody showed strong expression of VSTM2A in normal epithelium compared with paired tumor regions in the same patients (FIG. 12). Significant reduction of VSTM2A proteins was found in 18 out of 19 tumor tissue samples (95%) compared with paired nontumor tissues from CRC patients (FIG. 12). To further explore the clinical relevance of VSTM2A, we evaluated the association between VSTM2A expression levels in tumor from CRC patients and their clinical outcomes by tissue microarray. The tumors were categorized into high and low expression groups based on a scoring system of the VSTM2A staining assessed by two independent pathologists A survival analysis of 158 CRC patients indicated that high VSTM2A staining was significantly correlated with longer overall survival and disease-free survival (FIG. 13).

Figure 14:
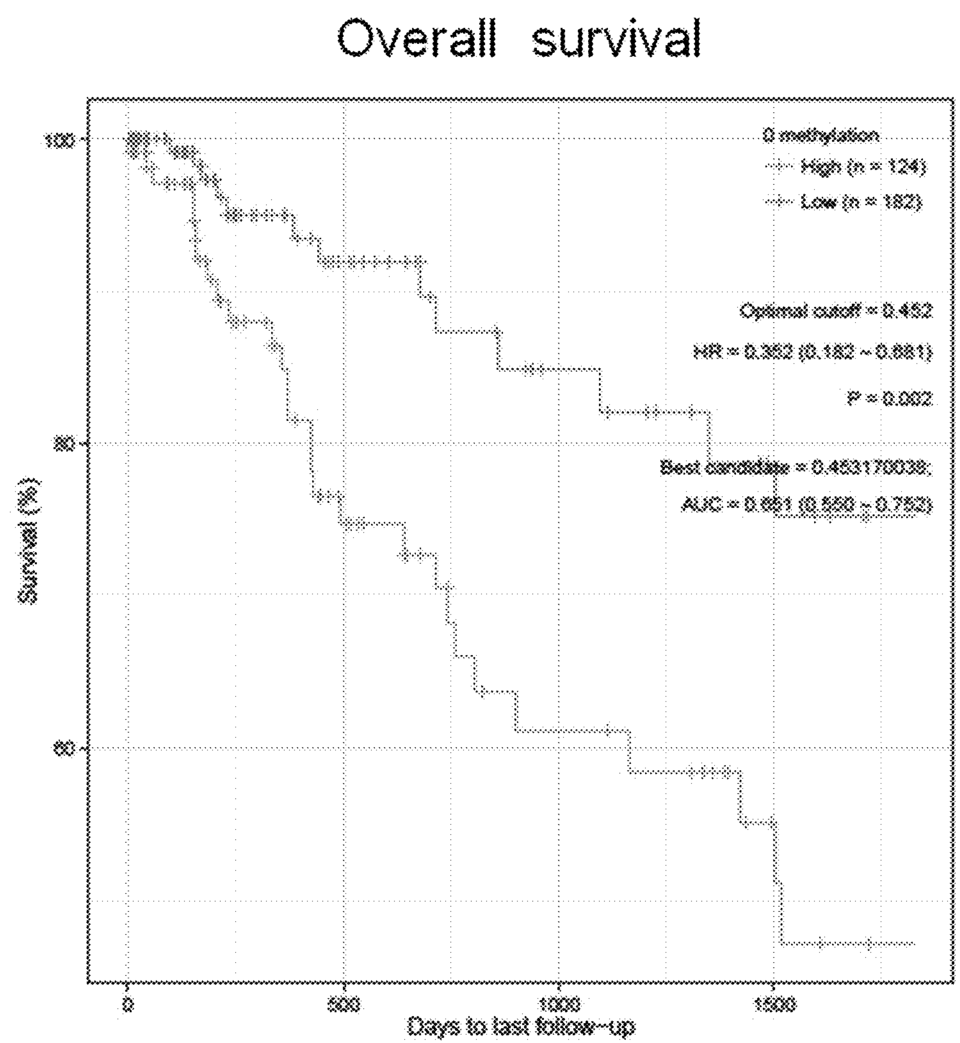
FIG. 14 shows VSTM2A methylation is an independent prognostic factor of poor outcome in patients with colorectal cancer in an embodiment.

Promoter Methylation of VSTM2A is an Independent Prognostic Factor of Poor Outcome in Patients with Colorectal Cancer The association of VSTM2A methylation status and clinicopathological features including clinical outcome was analysed in 306 patients with colorectal cancer from TCGA data set. High methylated VSTM2A was detected in 50.5% of primary colorectal cancers (124 of 306). We further examined the prognostic factors of colorect cancer patients. Univariate Cox regression analysis suggested that VSTM2A methylation was associated with a significant increased risk of cancer-related death. The relative risk (RR) was 2.87 with 95% confidence interval (CI) ranging from 1.57 to 5.26 (P=0.010, Table 3). After the adjustment for potential confounding factors, multivariate Cox regression analysis showed that VSTM2A methylation was an independent predictor of poorer survival of colorectal cancer patients (RR 2.79, 95% CI 1.50 to 5.18; P=0.01, Table 3). Kaplan-Meier survival curves showed that colorectal cancer patients with VSTM2A methylation had significantly poorer overall survival than patients without methylation based on the log-rank test (P<0.01; FIG. 14).

All patents, patent applications, and other publications, including GenBank Accession Numbers, cited in this application are incorporated by reference in the entirety for all purposes.

TABLE 1

| DNA sequences of primers used in this study. | | |
|---|---|---|
| Primer | Name | Sequence (5'-3') |
| Real-time PCR primers for detecting VSTM2A mRNA expression: | | |
| VSTM2A-all-F | GGACCAAGATCAGCACAGTGAA | SEQ. ID. NO. 1 |
| VSTM2A-all-R | TCATCCTTTTTCCTCACTTTGGA | SEQ. ID. NO. 2 |
| VSTM2A-iso1-F | ACCTCCAGCCCTCAAGTGGTA | SEQ. ID. NO. 3 |
| VSTM2A-iso1-R | CCTTTCTGTGGAGCGTTTGTG | SEQ. ID. NO. 4 |
| VSTM2A-iso2-F | TCTCCAATCCTTCCAGAAGTCAA | SEQ. ID. NO. 5 |
| VSTM2A-iso2-R | TCTGTGTGACGTTGGGAAGGT | SEQ. ID. NO. 6 |
| VSTM2A-iso3-F | ACCTCCAGCCCTCAAGTGGTA | SEQ. ID. NO. 7 |
| VSTM2A-iso3-R | ACAAAGCCACAAACAAGAAGCA | SEQ. ID. NO. 8 |
| VSTM2A-iso4-F | ACAATCAGCAAAGAGCAAATCG | SEQ. ID. NO. 9 |
| VSTM2A-iso4-R | GCAGGCGCTCCTTGTGTAGT | SEQ. ID. NO. 10 |
| β-actin-F | GTCTTCCCCTCCATCGTG | SEQ. ID. NO. 11 |
| β-actin-R | AGGGTGAGGATGCCTCTCTT | SEQ. ID. NO. 12 |
| Semi-quantitative PCR primers: | | |
| VSTM2A-semi-F | CTCGGTGTATCTGGAGATCCAAT | SEQ. ID. NO. 13 |
| VSTM2A-semi-R | CCCGTAGTTGGCATCAGTCA | SEQ. ID. NO. 14 |
| BGS primers: | | |
| VSTM2A-BGS-F | TGTTTTTTAGAAGGGAGATTTTAG | SEQ. ID. NO. 15 |
| VSTM2A-BGS-R | TACCTAACTACCTACTTTCAACTACCTAAC | SEQ. ID. NO. 16 |

Abbreviations: PCR: polymerase chain reaction; BGS, bisulfite genomic sequencing.

TABLE 2

Target sequences used in this study

1) SEQ ID NO: 17: Sequence of promoter CpG island region of human VSTM2A gene (chr7: 54542042-54542447, 406 bp)

CGGAACCTTTTGCTCCGAGCCCCCCGCCAGCGCCGCAATCCCGTCACTGTATTGTCCTCCTCGGCACCGAGCGATCT
GATCCGCCGAGCCAGAAAGACACCCGATGGGGGAGAGAAGCAAAGTGGAAAAAAACCGACGTCCCTGCTCTCCAGAA
GGGAGACCCCAGCGGCGCCGACGAGCCCTGCGCCCTCCGCGGCCGCCCGGCGCGAGCTCCCGGGCGGGGCGCTGTCC
AGCGCGCACAGAGTTAAAGGCATCATCGCAGCCATTAGAGGGAAAAGTTGCGGCGCCGCGAGCCCGGCGAAGTCCTC
AGCCCGCCCCGCTTGCCCACTCCCCACTTCCCGAGCCGGCTCCGTGTTTAGGGAGGGCAGTGATCACGCAAGCCGGA
GCGGCGGGCTGACGTTGGACG

2) SEQ ID NO: 18: CCD575604.1: VSTM2A protein coding cDNA sequence (723 bp)

ATGATGGGGATCTTTTTGGTGTATGTTGGATTTGTTTTCTTTTCCGTTTTATATGTACAACAAGGGCTTTCTTCTCA
AGCAAAATTTACCGAGTTTCCGCGGAACGTGACGGCGACCGAGGGGCAGAATGTGGAGATGTCCTGCGCCTTCCAGA
GCGGCTCCGCCTCGGTGTATCTGGAGATCCAATGGTGGTTCCTGCGGGGGCCGGAGGACCTGGATCCCGGGGCCGAG
GGGGCCGGCGCGCAGGTGGAGCTCTTGCCCGACAGAGACCCGGACAGCGACGGGACCAAGATCAGCACAGTGAAAGT
CCAAGGCAATGACATCTCCCACAAGCTTCAGATTTCCAAAGTGAGGAAAAAGGATGAAGGCTTATATGAGTGCAGGG
TGACTGATGCCAACTACGGGGAGCTTCAGGAACACAAGGCCCAGGCCTATCTGAAAGTCAATGCCAACAGCCATGCC
CGCAGAATGCAGGCCTTCGAAGCCTCGCCCATGTGGCTGCAGGATATGAAGCCCCGCAAGAACGTCTCCGCAGCCAT
CCCCAGCAGCATCCATGGCTCTGCCAACCAACGAACGCACTCCACCTCCAGCCCTCAAGTGGTAGCCAAAATCCCCA
AACAAAGTCCACAATCAGCAAAGAGCAAATCGCCTGTAAAATCTACGGAGCGGACAGCAAAGTTGACCCTAAACTCC
AAGCACCACCCTGCACCCACTGTACTCTAA

3) SEQ ID NO: 19: VSTM2A mRNA sequence (Genbank: NM_001301009, 3000 bp)

GCGCCGCGAGCCCGGCGAAGTCCTCAGCCCGCCCCGCTTGCCCACTCCCCACTTCCCGAGCCGGCTCCGTGTTTAGG
GAGGGCAGTGATCACGCAAGCCGGAGCGGCGGGCTGACGTTGGACGAGCTGCCAGGTAGCTGAAAGCAGGCAGCCAG
GCAGCCGAGACACTTCCCAGCGATTCCAGCCTGGGCTCCGCAGGAAGCCTCGCTGAATCCCAGCCAGCTGGTTCTAA
CCTTCCAGAATCGCAATCCCTTCTCCCCACAGCCAGCCCTCGCCAAGCAAGCAGCAGGATGTTTGCAGTGTCGCGCC
CAGGGCTCTGAGACTGAGCCTGCCATCCACTCGCACGCCTTTCTTTCAGGGCTTTTCGGCTGTTGGCTACACTGATG
TGACCCCCCTCCCTTTTTGGAATGATGGGGATCTTTTTGGTGTATGTTGGATTTGTTTTCTTTTCCGTTTTATATGT
ACAACAAGGGCTTTCTTCTCAAGCAAAATTTACCGAGTTTCCGCGGAACGTGACGGCGACCGAGGGGCAGAATGTGG
AGATGTCCTGCGCCTTCCAGAGCGGCTCCGCCTCGGTGTATCTGGAGATCCAATGGTGGTTCCTGCGGGGGCCGGAG
GACCTGGATCCCGGGGCCGAGGGGGCCGGCGCGCAGGTGGAGCTCTTGCCCGACAGAGACCCGGACAGCGACGGGAC
CAAGATCAGCACAGTGAAAGTCCAAGGCAATGACATCTCCCACAAGCTTCAGATTTCCAAAGTGAGGAAAAAGGATG
AAGGCTTATATGAGTGCAGGGTGACTGATGCCAACTACGGGGAGCTTCAGGAACACAAGGCCCAGGCCTATCTGAAA
GTCAATGCCAACAGCCATGCCCGCAGAATGCAGGCCTTCGAAGCCTCGCCCATGTGGCTGCAGGATATGAAGCCCCG
CAAGAACGTCTCCGCAGCCATCCCCAGCAGCATCCATGGCTCTGCCAACCAACGAACGCACTCCACCTCCAGCCCTC
AAGTGGTAGCCAAAATCCCCAAACAAAGTCCACAATCAGCAAAGAGCAAATCGCCTGTAAAATCTACGGAGCGGACA
GCAAAGTTGACCCTAAACTCCAAGCACCACCCTGCACCCACTGTACTCTAATTCACTACACAAGGAGCGCCTGCTTC
CGGAAGCATAAATGAAGAGGCTATCACATGCTTTGTTGATCATATTTTCTTTGGCAAAACACTGATCTTTTATTTTA
AGAGAATTAACGTGAAGTGATAGAACGTTTTCTAATAGCAAGATCTATTTTTTCCCTTTTCTTTCGGCGACTAAAAT
CATCTCACTGACTGCTCAAGGGTTGGCCTGAATGTCATCAGGATAGGGAATATTTACTATGGATACCACTAATTTCC
TACTAAAGGACCCAGCATCTTCAGGAAGCAAACAGAGATCAAAAGGCTACAGAACAGAAGCTATCATCAGACAAAAC
CCCCTTTTTAGGGGAAGAACAAAACTATCAACACTGCAAGTCAACAAGGAGGACATTACTTTAAGGAATAACATGAG

TABLE 2-continued

| Target sequences used in this study |
| --- |
| AAAGAAATTTTTTTATTTTCCCCTTTTTTTCTTGGATTTTTCTTCTTTTTCTTGATTACAGTTCTTGTTCAATGGTG<br>GCAAGTGCTGGTTATGGCCAATCTCCGTCAATCCTAGGAGGTTTATAGAACTACATTTTGAGTGTTCTATATTTCAG<br>TGTATTTTAATTCATTTTGCAATTCCTGTGTATGCAAACCTGATAAATTCTGTAAATTGCTTATAGTATGTGTGCTA<br>TAACTTCAAAGTAGATGTACTGCGACCCTCATGCAAGCTGATTTTTATCATTATATATATAAATATATACTTAAGAA<br>TATCTGTGTGTTGGGCCAATGACCAACTTTTTTTGACGAAGCATTTGTTTTTCGTTGATAATTCATACACTGCGTGA<br>ATTTTGTAATTCATTGTTTCACTTCCACAGGTTTGACAGCTGCAGATGGTCTCTATTGTCCTCTGCTTCATTCTGGA<br>AAGTGCATATTCAAAATTGTATCAGTCTCTGATCGATGAATTAATTTTGTTATGTCTGTGCTAAGTTGGAATTTACT<br>ATGTTCCTTTATACATGGTGTTTATTGAGGTTTGAGAGTCTCTTGACTGTGAAGAATGTACACTGTCTGGTTTTGAC<br>AGCTATTTCTGTATTATTATCATTATAATCTTGTCAAATAGAAATGTTGCTTCTAGAAAATTTGCCTAGGAGGCGAA<br>TGTGGGGAAGGTGAAGCACTCACCATAATTCCCTAAATTCATGTTAGAACATTTCTTGCTATGGTTAAAAATGCTGC<br>TTCCTTTGACCTTTATGAATTTCTGTACCTTTGTCATTCTGTTACCTTTGTCATTCTGTTATTTGCGCTAATTATAT<br>TTTAATGTCTCCTAATTAAAAATTAAAATTTGGTTGTTGGCTAAATACAATATGCAAAAGATGATGGCAGGTCCCCG<br>ACTAAAGAAGATTAATGTGTTCAGTTTTCACTGGTTAAGTGAATTATAATTTTAAATATTCCATTCTTATTTATGTC<br>TTTATGATAATTCAGACTATTTTATTTTGAACCTGTTTTCTACTCTGGCAAAGAAAGATAGGCAGAACTATTAGTGT<br>TCCATATACATTATGGAATAGATAAAGCTTGAGAGATAAATGACCTAAGTTTTCCTTCCAGAGAGACTCTTCCATTT<br>TCTCTCATTACAAAACCAGAAGATCAGCTATGTGGGGCCATCAGCTCCCAGCCTAAGGTCCTATAACCCGAAGCTTG<br>AAGGCAATCAGTACCTCTGCTTTTCAAAGGTAAATGCATTCATTTTCTTTGATTCAGTTATAAGCAAGTATATATTT<br>TCATAATATTCTTGACATTACCTGAGAAATAATACTTCATGCTAAATCTTTTACTGCCACTTTTCTCATTCATTTGG<br>TTTATCATTTCAGTTTAATGAGAAAAATTAATAAAGGTTTTGATTGCACTATTTTATTAACCTAAAAAAAAAAA |
| 4) SEQ ID NO: 20: Partial coding sequence used to detect human VSTM2A all isoforms by real-time PCR (82 bp).<br>GGACCAAGATCAGCACAGTGAAAGTCCAAGGCAATGACATCTCCCACAAGCTTCAGATTTCCAAAGTGAGGAAAAAG<br>GATGA |
| 5) SEQ ID NO: 21: Partial coding sequence used to detect human VSTM2A isoform 1by real-time PCR (153 bp).<br>ACCTCCAGCCCTCAAGTGGTAGCCAAAATCCCCAAACAAAGTCCACAATCAGGTATGGAAACCCATTTCGAGCCTTT<br>TATTTTACCACTCACAAACGCTCCACAGAAAGGTCAGTCGTATAGAGTAGACAGATTTATGAATGGTGATTTTTAA |
| 6) SEQ ID NO: 22: Partial coding sequence used to detect human VSTM2A isoform 2 by real-time PCR (120 bp).<br>TCTCCAATCCTTCCAGAAGTCAAACATCTCCACAGACCACCTCTACTAGTCCTTCCTTTCTTCTCTCTGTCTTCACT<br>TTTTTCTACTGACCCCCTTCCCACCTTCCCAACGTCACACAGA |
| 7) SEQ ID NO: 23: Partial coding sequence used to detect human VSTM2A isoform 3 by real-time PCR (110 bp).<br>ACCTCCAGCCCTCAAGTGGTAGCCAAAATCCCCAAACAAAGTCCACAATCAGGTGCGAGGATAGCTACAAGCCATGG<br>ACTTTCTGTCCTGCTTCTTGTTTGTGGCTTTGT |
| 8) SEQ ID NO: 24: Partial coding sequence used to detect human VSTM2A isoform 4 by real-time PCR (120 bp).<br>ACAATCAGCAAAGAGCAAATCGCCTGTAAAATCTACGGAGCGGACAGCAAAGTTGACCCTAAACTCCAAGCACCACC<br>CTGCACCCACTGTACTCTAATTCACTACACAAGGAGCGCCTGC |
| 9) SEQ ID NO: 25: Partial coding sequence used to detect human VSTM2A by semi-quantitative PCR (241 bp).<br>CTCGGTGTATCTGGAGATCCAATGGTGGTTCCTGCGGGGGCCGGAGGACCTGGATCCCGGGGCCGAGGGGGCCGGCG<br>CGCAGGTGGAGCTCTTGCCCGACAGAGACCCGGACAGCGACGGGACCAAGATCAGCACAGTGAAAGTCCAAGGCAAT<br>GACATCTCCCACAAGCTTCAGATTTCCAAAGTGAGGAAAAAGGATGAAGGCTTATATGAGTGCAGGGTGACTGATGC<br>CAACTACGGG |
| 10) SEQ ID NO: 26: NP_001287938: VSTM2A *Homo sapiens*, 240 amino acids.<br>MMGIFLVYVGFVFFSVLYVQQGLSSQAKFTEFPRNVTATEGQNVEMSCAFQSGSASVYLEIQWWFLRGPEDLDPGAE<br>GAGAQVELLPDRDPDSDGTKISTVKVQGNDISHKLQISKVRKKDEGLYECRVTDANYGELQEHKAQAYLKVNANSHA<br>RRMQAFEASPMWLQDMKPRKNVSAAIPSSIHGSANQRTHSTSSPQVVAKIPKQSPQSAKSKSPVKSTERTAKLTLNS<br>KHHPAPTVL |

TABLE 3

Univariate and multivariate Cox regression analysis of potential poor prognostic factors in 306 colorectal cancer patients

| | Univariate | | Multivariate | |
| --- | --- | --- | --- | --- |
| Variable | RR (95% CI) | P-vaule | RR (95% CI) | P-value |
| Age | 1.01 (0.99-1.03) | 0.229 | 1.02 (0.99-1.04) | 0.130 |
| Gender | | | | |
| Male | 2.53 (1.36-4.72) | 0.040 | 1.90 (0.99-3.64) | 0.055 |
| Female | 1.00 | | 1.00 | |

TABLE 3-continued

Univariate and multivariate Cox regression analysis of potential poor prognostic factors in 306 colorectal cancer patients

| | Univariate | | Multivariate | |
| --- | --- | --- | --- | --- |
| Variable | RR (95% CI) | P-vaule | RR (95% CI) | P-value |
| Lymph metastasis | | | | |
| Yes | 1.79 (1.00-3.19) | 0.049 | 0.43 (0.94-1.93) | 0.267 |
| No | 1.00 | | 1.00 | |
| TNM stage | | | | |
| I | 0.26 (0.07-0.87) | 0.030 | 0.08 (0.01-0.58) | 0.012 |
| II | 0.23 (0.13-0.47) | 0.001 | 0.09 (0.02-0.43) | 0.003 |

TABLE 3-continued

Univariate and multivariate Cox regression analysis of potential poor prognostic factors in 306 colorectal cancer patients

| | Univariate | | Multivariate | |
|---|---|---|---|---|
| Variable | RR (95% CI) | P-vaule | RR (95% CI) | P-value |
| III | 0.30 (0.14-0.62) | 0.001 | 0.30 (0.14-0.65) | 0.002 |
| IV | 1.00 | | 1.00 | |
| VSTM2A methylation | | | | |
| Methylated | 2.87 (1.57-5.26) | 0.010 | 2.79(1.50-5.18) | 0.010 |
| Unmethylated | 1.00 | | 1.00 | |

LIST OF REFERENCES

1. CHOI I S and WU T T. Epigenetic alterations in gastric carcinogenesis. *Cell Research* 2005, 15: 247-254.
2. Livak K J, Schmittgen T D. Analysis of relative gene expression data using real-time quantitative PCR and the 2(-Delta Delta C(T)) Method. *Methods* 2001, 25: 402-408.
3. Takai D, Jones P A. Comprehensive analysis of CpG islands in human chromosomes 21 and 22. *Proc Natl Acad Sci USA* 2002, 99: 3740-3745.
4. Takai D, Jones P A. The CpG island searcher: a new WWW resource. *In Silico Biol* 2003, 3: 235-240.

What is claimed is:

1. A method for assessing risk for colorectal cancer in a human subject, comprising the steps of:

(a) treating genomic DNA from a colorectal sample taken from the subject with a bisulfate;

(b) performing a polymerase chain reaction (PCR) using a primer comprising nucleotide sequence of SEQ ID NO:15 or 16 to determine number of methylated CpGs in a genomic sequence, which is the 167-319 segment of SEQ ID NO:17 or a fragment thereof comprising at least 5 CpGs, and (c) comparing the number of methylated CpGs from step (b) with the number of methylated CpGs in the same genomic sequence, which is taken from a human non-cancer colorectal sample and has been processed through steps (a) and (b); and (d) determining the human subject, whose colorectal sample contains more methylated CpGs in the genomic sequence determined in step (b) compared to the number of methylated CpGs with the number of methylated CpGs in the same genomic sequence from a human non-cancer colorectal sample and having been processed through steps (a) and (b), as having an increased risk for colorectal cancer compared with a healthy human subject not diagnosed with colorectal cancer.

2. The method of claim 1, wherein the colorectal sample is a colon mucosa sample.

3. The method of claim 1, wherein the genomic sequence is the 167-319 segment of SEQ ID NO:17.

4. The method of claim 1, wherein the bisulfite is sodium bisulfite.

5. The method of claim 1, wherein primers consisting of nucleotide sequences of SEQ ID NOs:15 and 16 are used in the PCR.

6. A method for assessing likelihood of mortality from colorectal cancer in a human colorectal cancer patient, comprising the steps of:

(a) treating genomic DNA from a colorectal cancer sample taken from a first human colorectal cancer patient with a bisulfite;

(b) performing a polymerase chain reaction (PCR) using a primer comprising nucleotide sequence of SEQ ID NO:15 or 16 to determine number of methylated CpGs in a genomic sequence, which is the 167-319 segment of SEQ ID NO:17 or a fragment thereof comprising at least 5 CpGs, and (c) comparing the number of methylated CpGs from step (b) with the number of methylated CpGs in the same genomic sequence, which is taken from another colorectal cancer sample of the same type obtained from a second human colorectal cancer patient and has been processed through steps (a) and (b); and (d) determining the first human patient, whose colorectal cancer sample contains more methylated CpGs in the genomic sequence determined in step (b) compared to the number of methylated CpGs with the number of methylated CpGs in the same genomic sequence taken from the colorectal cancer sample obtained from the second human patient and having been processed through steps (a) and (b), as having an increased likelihood of mortality from colorectal cancer compared with the second human colorectal cancer patient.

7. The method of claim 6, wherein the colorectal sample is a colon mucosa sample.

8. The method of claim 6, wherein the genomic sequence is the 167-319 segment of SEQ ID NO:17.

9. The method of claim 6, wherein the bisulfite is sodium bisulfite.

10. The method of claim 6, wherein primers consisting of nucleotide sequences of SEQ ID NOs:15 and 16 are used in the PCR.

* * * * *